United States Patent
Van Der Burg et al.

(10) Patent No.: US 11,458,198 B2
(45) Date of Patent: Oct. 4, 2022

(54) HPV EPITOPES TARGETED BY T CELLS INFILTRATING CERVICAL MALIGNANCIES FOR USE IN VACCINES

(71) Applicant: Academisch Ziekenhuis Leiden H.O.D.N. LUMC, Leiden (NL)

(72) Inventors: Sjoerd Henricus Van Der Burg, Leiden (NL); Gemma G. Kenter, Amsterdam (NL); Cornelis Johannes Maria Melief, Haarlem (NL)

( * ) Notice: Subject to any disclaimer, the term of this patent is extended or adjusted under 35 U.S.C. 154(b) by 163 days.

(21) Appl. No.: 16/884,505

(22) Filed: May 27, 2020

(65) Prior Publication Data
US 2020/0289640 A1 Sep. 17, 2020

Related U.S. Application Data

(63) Continuation of application No. 16/287,559, filed on Feb. 27, 2019, now Pat. No. 10,688,173, which is a continuation of application No. 15/678,970, filed on Aug. 16, 2017, now Pat. No. 10,258,684, which is a continuation of application No. 14/453,286, filed on Aug. 6, 2014, now Pat. No. 9,764,023, which is a continuation of application No. 12/592,528, filed on Feb. 16, 2010, now abandoned, which is a continuation of application No. PCT/NL2008/050320, filed on May 27, 2008.

(60) Provisional application No. 60/941,070, filed on May 31, 2007.

(30) Foreign Application Priority Data

May 31, 2007 (EP) ..................... 07109281
May 31, 2007 (EP) ..................... 07109287

(51) Int. Cl.
| | |
|---|---|
| A61K 39/12 | (2006.01) |
| C07K 14/005 | (2006.01) |
| C12N 7/00 | (2006.01) |
| A61K 39/00 | (2006.01) |
| A61K 38/00 | (2006.01) |

(52) U.S. Cl.
CPC ............ *A61K 39/12* (2013.01); *C07K 14/005* (2013.01); *C12N 7/00* (2013.01); *A61K 38/00* (2013.01); *A61K 2039/585* (2013.01); *C12N 2710/20022* (2013.01); *C12N 2710/20034* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 5,629,161 A | 5/1997 | Muller et al. | |
| 5,932,412 A | 8/1999 | Dillner et al. | |
| 6,419,931 B1 | 7/2002 | Vitiello et al. | |
| 6,783,763 B1 | 8/2004 | Choppin et al. | |
| 7,399,467 B2 | 7/2008 | Lu et al. | |
| 8,252,893 B2 | 8/2012 | Kim et al. | |
| 8,628,779 B2 | 1/2014 | Preville | |
| 8,652,482 B2 | 2/2014 | Nakagawa | |
| 9,562,075 B2* | 2/2017 | Van Der Burg | ......... C12N 7/00 |
| 9,764,023 B2 | 9/2017 | Van Der Burg et al. | |
| 2004/0091479 A1 | 5/2004 | Nieland et al. | |
| 2004/0151723 A1 | 8/2004 | Maeda et al. | |
| 2004/0170644 A1 | 9/2004 | Mailere et al. | |
| 2005/0142541 A1 | 6/2005 | Lu et al. | |
| 2006/0002941 A1 | 1/2006 | Mahairas et al. | |
| 2006/0182763 A1 | 8/2006 | Kim et al. | |

FOREIGN PATENT DOCUMENTS

| | | |
|---|---|---|
| DE | 19737409 | 3/1999 |
| WO | WO-01/21645 | 3/2001 |
| WO | WO-02/44384 A2 | 6/2002 |
| WO | WO-02/070006 A2 | 9/2002 |
| WO | WO-2005/060993 A1 | 7/2005 |
| WO | WO-2005/063286 | 7/2005 |

OTHER PUBLICATIONS

Altmann, et al. "Definition of Immunogenic Determinants of the Human Papillomavirus Type 16 Nucleoprotein E7", Eur J Cancer (1992), vol. 28, No. 2/3, pp. 326-333.

De Jong, et al. "Rapid enrichment of human papillomavirus (HPV)-specific polyclonal T cell populations for adoptive immunotherapy of cervical cancer", Int. J. Cancer (2005), vol. 114, pp. 274-282.

Haegert, et al. "Sequence variation in the E6 gene of human papillomavirus type 16", (Nov. 1, 1996), Database Accession No. Q80882 (Abstract).

Hohn, et al. "CD4 Tumor-Infiltrating Lymphocytes in Cervical Cancer Recognize HLA-DR-Restricted Peptides Provided by Human Papillomavirus-E7", The Journal of Immunology, (1999), vol. 163, pp. 5715-5722.

Hohn, et al. "Human Papillomavirus Type 33 E7 Peptides Presented by HLA-DR *0402 to Tumor-Infiltrating T Cells in Cervical Cancer", Journal of Virology, (Jul. 2000), vol. 74, No. 14, pp. 6632-6636.

(Continued)

*Primary Examiner* — Agnieszka Boesen
(74) *Attorney, Agent, or Firm* — Foley & Lardner LLP

(57) ABSTRACT

The present invention relates to novel CD4+ and CD8+ T cell epitopes that are specific for HPV-specific E6 and E7 oncoproteins, to peptides comprising these novel T cell epitopes, and to (vaccine) compositions comprising these peptides for use in methods for the prevention and/or treatment of HPV related diseases. Preferred epitopes are recognized by a T cell that infiltrates a cervical neoplastic lesion or by a T cell from a draining lymph node, and are presented by an HLA-DQ or HLA-DP molecule, or an HLA-B.

19 Claims, 13 Drawing Sheets

Specification includes a Sequence Listing.

(56) References Cited

OTHER PUBLICATIONS

Watts et al., "E6 Protein" Accession No. Q919B2, Dec. 1, 2001.
Kadish, et al. "Lymphoproliferative Responses to Human Papillomavirus (HPV) Type 16 Proteins E6 and E7: Outcome of HPV Infection and Associated Neoplasia", Journal of the National Cancer Institute (Sep. 3, 1997), vol. 89, No. 17, pp. 1285-1293.
Kaisho et al., "Toll-like receptors as adjuvant receptors", Biochimica et Biophysica Acta 1589 (2002), pp. 1-13.
Kast et al., "Role of HLA-A Motifs in identification of potential CTL epitopes in human papillomavirus Type 16 E6 and E7 proteins" Journal of Immunology, 1994, vol. 152, pp. 3904-3912.
Ma et al., "Human papillomavirus type 16 early transforming protein E6 variant (E6) gene, complete cds" Accession No. AF327851, Dec. 12, 2000.
Nakagawa, et al. "T-cell proliferative response to human papillomavirus type 16 peptides: relationship to cervical intraepithelial neoplasia", Clinical Diagn. Lab. Immunology (1996), vol. 3, No. 2, pp. 205-210.
Peng, et al. "HLA-DQB1 *02-Restricted HPV-16 E7 Peptide-Specific CD4+ T-Cell Immunie Responses Correlate with Regression of HPV-16-Associated High-Grade Squamous Intraepithelial Lesions", Clin Cancer Res, Apr. 15, 2007, vol. 13, No. 8, pp. 2479-2487.
Strang, et al. "Human T cell responses to human papillomavirus type 16 L1 and E6 synthetic peptides: identification of T cell determinants, HLA-DR restriction and virus type specificity", Journal of General Virology (1990) vol. 71, pp. 423-431.
Vambutas, et al. "Therapeutic vaccination with papillomavirus E6 and E7 long peptides results in the control of both established virus-induced lesions and latently infected sites in a pre-clinical cottontail rabbit papillomavirus model", Vaccine, (2005), vol. 23, pp. 5271-5280.
Van Der Burg, et al. "Natural T-Helper Immunity Against Human Papillomavirus Type 16 (HPV16) E7-Derived Peptide Epitopes in Patients with HPV16-Positive Cervical Lesions: Identification of 3 Human Leukocyte Antigen Class II-Restricted Epitopes", Int. J. Cancer, (2001), vol. 91, pp. 612-618.
Watts, et al. "Sequence variation and physical state of human papillomavirus type 16 cervical cancer isolates from Australia and New Caledonia", International Journal of Cancer (2002), vol. 97, Issue 6, pp. 868-874.
Zwaveling, et al. "Established Human Papillomavirus Type 16-Expressing Tumors Are Effectively Eradicated Following Vaccination with Long Peptides", The Journal of Immunology, (2002), vol. 169, pp. 350-358.
Evans, et al. "Infiltration of Cervical Cancer Tissue with Human Papillomavirus-specific Cytotoxic T-Lymphocytes", Cancer Research, (Jul. 154, 1997), vol. 57, pp. 2943-2950.
Knapp et al., "Identification of the Nuclear Localization and Export Signals of High Risk HPV16 E7 Oncoprotein", Virology, vol. 383, No. 1, 2009, pp. 1-24, Author Manuscript (24 pages).

* cited by examiner

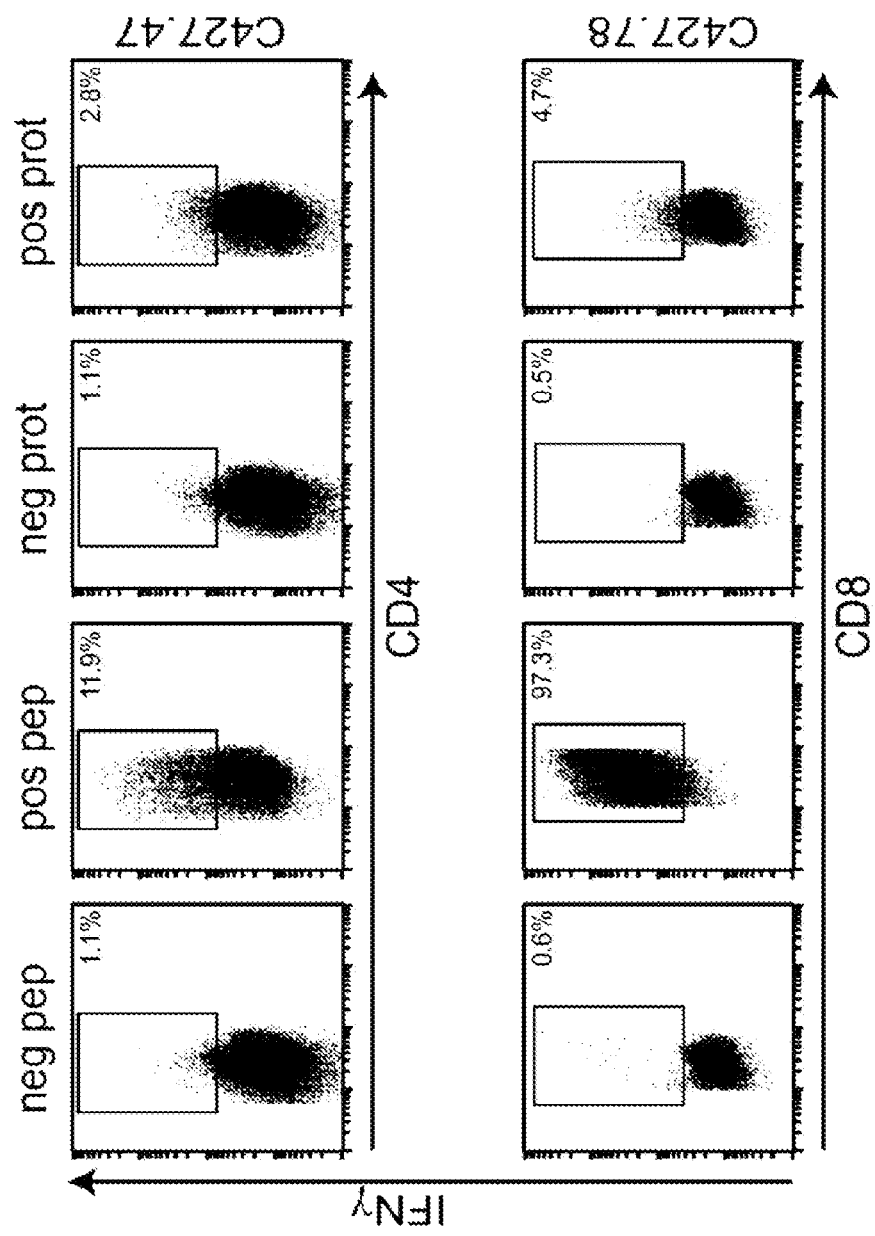

SEQUENCE LISTING

```
<160> NUMBER OF SEQ ID NOS: 39

<210> SEQ ID NO 1
<211> LENGTH: 158
<212> TYPE: PRT
<213> ORGANISM: Human papillomavirus type 16

<400> SEQUENCE: 1

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 2
<211> LENGTH: 98
<212> TYPE: PRT
<213> ORGANISM: Human papillomavirus type 16

<400> SEQUENCE: 2

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60
```

```
Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 3
<211> LENGTH: 158
<212> TYPE: PRT
<213> ORGANISM: Human papillomavirus type 18

<400> SEQUENCE: 3

Met Ala Arg Phe Glu Asp Pro Thr Arg Arg Pro Tyr Lys Leu Pro Asp
  1               5                  10                  15

Leu Cys Thr Glu Leu Asn Thr Ser Leu Gln Asp Ile Glu Ile Thr Cys
                 20                  25                  30

Val Tyr Cys Lys Thr Val Leu Glu Leu Thr Glu Val Phe Glu Phe Ala
             35                  40                  45

Phe Lys Asp Leu Phe Val Val Tyr Arg Asp Ser Ile Pro His Ala Ala
 50                  55                  60

Cys His Lys Cys Ile Asp Phe Tyr Ser Arg Ile Arg Glu Leu Arg His
 65                  70                  75                  80

Tyr Ser Asp Ser Val Tyr Gly Asp Thr Leu Glu Lys Leu Thr Asn Thr
                 85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
            115                 120                 125

Asn Ile Ala Gly His Tyr Arg Gly Gln Cys His Ser Cys Cys Asn Arg
        130                 135                 140

Ala Arg Gln Glu Arg Leu Gln Arg Arg Arg Glu Thr Gln Val
145                 150                 155

<210> SEQ ID NO 4
<211> LENGTH: 105
<212> TYPE: PRT
<213> ORGANISM: Human papillomavirus type 18

<400> SEQUENCE: 4

Met His Gly Pro Lys Ala Thr Leu Gln Asp Ile Val Leu His Leu Glu
  1               5                  10                  15

Pro Gln Asn Glu Ile Pro Val Asp Leu Leu Cys His Glu Gln Leu Ser
                 20                  25                  30

Asp Ser Glu Glu Glu Asn Asp Glu Ile Asp Gly Val Asn His Gln His
             35                  40                  45

Leu Pro Ala Arg Arg Ala Glu Pro Gln Arg His Thr Met Leu Cys Met
 50                  55                  60

Cys Cys Lys Cys Glu Ala Arg Ile Glu Leu Val Val Glu Ser Ser Ala
 65                  70                  75                  80

Asp Asp Leu Arg Ala Phe Gln Gln Leu Phe Leu Asn Thr Leu Ser Phe
                 85                  90                  95

Val Cys Pro Trp Cys Ala Ser Gln Gln
            100                 105

<210> SEQ ID NO 5
<211> LENGTH: 22
```

```
<212> TYPE: PRT
<213> ORGANISM: Human papillomavirus type 16

<400> SEQUENCE: 5

Asp Pro Gln Glu Arg Pro Arg Lys Leu Pro Gln Leu Cys Thr Glu Leu
1               5                   10                  15

Gln Thr Thr Ile His Asp
            20

<210> SEQ ID NO 6
<211> LENGTH: 32
<212> TYPE: PRT
<213> ORGANISM: Human papillomavirus type 16

<400> SEQUENCE: 6

Cys Val Tyr Cys Lys Gln Gln Leu Leu Arg Arg Glu Val Tyr Asp Phe
1               5                   10                  15

Ala Phe Arg Asp Leu Cys Ile Val Tyr Arg Asp Gly Asn Pro Tyr Ala
            20                  25                  30

<210> SEQ ID NO 7
<211> LENGTH: 10
<212> TYPE: PRT
<213> ORGANISM: Human papillomavirus type 16

<400> SEQUENCE: 7

Phe Ala Phe Arg Asp Leu Cys Ile Val Tyr
1               5                   10

<210> SEQ ID NO 8
<211> LENGTH: 32
<212> TYPE: PRT
<213> ORGANISM: Human papillomavirus type 16

<400> SEQUENCE: 8

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile Ser Glu Tyr Arg His Tyr
            20                  25                  30

<210> SEQ ID NO 9
<211> LENGTH: 22
<212> TYPE: PRT
<213> ORGANISM: Human papillomavirus type 16

<400> SEQUENCE: 9

Tyr Arg Asp Gly Asn Pro Tyr Ala Val Cys Asp Lys Cys Leu Lys Phe
1               5                   10                  15

Tyr Ser Lys Ile Ser Glu
            20

<210> SEQ ID NO 10
<211> LENGTH: 33
<212> TYPE: PRT
<213> ORGANISM: Human papillomavirus type 16

<400> SEQUENCE: 10

Cys Leu Lys Phe Tyr Ser Lys Ile Ser Glu Tyr Arg His Tyr Cys Tyr
1               5                   10                  15

Ser Leu Tyr Gly Thr Thr Leu Glu Gln Gln Tyr Asn Lys Pro Leu Cys
            20                  25                  30

Asp
```

```
<210> SEQ ID NO 11
<211> LENGTH: 22
<212> TYPE: PRT
<213> ORGANISM: Human papillomavirus type 16

<400> SEQUENCE: 11

Tyr Gly Thr Thr Leu Glu Gln Gln Tyr Asn Lys Pro Leu Cys Asp Leu
1               5                   10                  15

Leu Ile Arg Cys Ile Asn
            20

<210> SEQ ID NO 12
<211> LENGTH: 22
<212> TYPE: PRT
<213> ORGANISM: Human papillomavirus type 16

<400> SEQUENCE: 12

Lys Pro Leu Cys Asp Leu Leu Ile Arg Cys Ile Asn Cys Gln Lys Pro
1               5                   10                  15

Leu Cys Pro Glu Glu Lys
            20

<210> SEQ ID NO 13
<211> LENGTH: 22
<212> TYPE: PRT
<213> ORGANISM: Human papillomavirus type 16

<400> SEQUENCE: 13

Glu Lys Gln Arg His Leu Asp Lys Lys Gln Arg Phe His Asn Ile Arg
1               5                   10                  15

Gly Arg Trp Thr Gly Arg
            20

<210> SEQ ID NO 14
<211> LENGTH: 10
<212> TYPE: PRT
<213> ORGANISM: Human papillomavirus type 16

<400> SEQUENCE: 14

Lys Gln Arg Phe His Asn Ile Arg Gly Arg
1               5                   10

<210> SEQ ID NO 15
<211> LENGTH: 22
<212> TYPE: PRT
<213> ORGANISM: Human papillomavirus type 16

<400> SEQUENCE: 15

Asp Leu Tyr Cys Tyr Glu Gln Leu Asn Asp Ser Ser Glu Glu Glu Asp
1               5                   10                  15

Glu Ile Asp Gly Pro Ala
            20

<210> SEQ ID NO 16
<211> LENGTH: 22
<212> TYPE: PRT
<213> ORGANISM: Human papillomavirus type 16

<400> SEQUENCE: 16

His Tyr Asn Ile Val Thr Phe Cys Cys Lys Cys Asp Ser Thr Leu Arg
1               5                   10                  15
```

```
Leu Cys Val Gln Ser Thr
            20

<210> SEQ ID NO 17
<211> LENGTH: 11
<212> TYPE: PRT
<213> ORGANISM: Human papillomavirus type 16

<400> SEQUENCE: 17

Ile Arg Thr Leu Glu Asp Leu Leu Met Gly Thr
1               5                   10

<210> SEQ ID NO 18
<211> LENGTH: 22
<212> TYPE: PRT
<213> ORGANISM: Human papillomavirus type 18

<400> SEQUENCE: 18

Arg Glu His Gly Ile Gln Thr Leu Asn His Gln Val Val Pro Ala Tyr
1               5                   10                  15

Asn Ile Ser Lys Ser Lys
            20

<210> SEQ ID NO 19
<211> LENGTH: 22
<212> TYPE: PRT
<213> ORGANISM: Human papillomavirus type 18

<400> SEQUENCE: 19

Asp Lys Cys Leu Lys Phe Tyr Ser Lys Ile Ser Glu Tyr Arg His Tyr
1               5                   10                  15

Cys Tyr Ser Leu Tyr Gly
            20

<210> SEQ ID NO 20
<211> LENGTH: 32
<212> TYPE: PRT
<213> ORGANISM: Human papillomavirus type 18

<400> SEQUENCE: 20

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

<210> SEQ ID NO 21
<211> LENGTH: 22
<212> TYPE: PRT
<213> ORGANISM: Human papillomavirus type 18

<400> SEQUENCE: 21

Ile Pro Val Asp Leu Leu Cys His Glu Gln Leu Ser Asp Ser Glu Glu
1               5                   10                  15

Glu Asn Asp Glu Ile Asp
            20

<210> SEQ ID NO 22
<211> LENGTH: 10
<212> TYPE: PRT
<213> ORGANISM: Human papillomavirus type 16

<400> SEQUENCE: 22

Gln Glu Arg Pro Arg Lys Leu Pro Gln Leu
```

```
1               5                   10
```

<210> SEQ ID NO 23
<211> LENGTH: 10
<212> TYPE: PRT
<213> ORGANISM: Human papillomavirus type 16

<400> SEQUENCE: 23

```
Thr Ile His Asp Ile Ile Leu Glu Cys Val
1               5                   10
```

<210> SEQ ID NO 24
<211> LENGTH: 10
<212> TYPE: PRT
<213> ORGANISM: Human papillomavirus type 16

<400> SEQUENCE: 24

```
Gly Arg Trp Thr Gly Arg Cys Met Ser Cys
1               5                   10
```

<210> SEQ ID NO 25
<211> LENGTH: 10
<212> TYPE: PRT
<213> ORGANISM: Human papillomavirus type 16

<400> SEQUENCE: 25

```
Ser Ser Arg Thr Arg Arg Glu Thr Gln Leu
1               5                   10
```

<210> SEQ ID NO 26
<211> LENGTH: 9
<212> TYPE: PRT
<213> ORGANISM: Human papillomavirus type 16

<400> SEQUENCE: 26

```
Ile Val Leu His Leu Glu Pro Gln Asn
1               5
```

<210> SEQ ID NO 27
<211> LENGTH: 32
<212> TYPE: PRT
<213> ORGANISM: Human papillomavirus type 16

<400> SEQUENCE: 27

```
Met His Gln Lys Arg Thr Ala Met Phe Gln Asp Pro Gln Glu Arg Pro
1               5                   10                  15
Arg Lys Leu Pro Gln Leu Cys Thr Glu Leu Gln Thr Thr Ile His Asp
            20                  25                  30
```

<210> SEQ ID NO 28
<211> LENGTH: 32
<212> TYPE: PRT
<213> ORGANISM: Human papillomavirus type 16

<400> SEQUENCE: 28

```
Leu Pro Gln Leu Cys Thr Glu Leu Gln Thr Thr Ile His Asp Ile Ile
1               5                   10                  15
Leu Glu Cys Val Tyr Cys Lys Gln Gln Leu Leu Arg Arg Glu Val Tyr
            20                  25                  30
```

<210> SEQ ID NO 29
<211> LENGTH: 25
<212> TYPE: PRT
<213> ORGANISM: Human papillomavirus type 16

<400> SEQUENCE: 29

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 30
<211> LENGTH: 26
<212> TYPE: PRT
<213> ORGANISM: Human papillomavirus type 16

<400> SEQUENCE: 30

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25

<210> SEQ ID NO 31
<211> LENGTH: 25
<212> TYPE: PRT
<213> ORGANISM: Human papillomavirus type 16

<400> SEQUENCE: 31

Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25

<210> SEQ ID NO 32
<211> LENGTH: 25
<212> TYPE: PRT
<213> ORGANISM: Human papillomavirus type 16

<400> SEQUENCE: 32

His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25

<210> SEQ ID NO 33
<211> LENGTH: 32
<212> TYPE: PRT
<213> ORGANISM: Human papillomavirus type 16

<400> SEQUENCE: 33

Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30

<210> SEQ ID NO 34
<211> LENGTH: 32
<212> TYPE: PRT
<213> ORGANISM: Human papillomavirus type 16

<400> SEQUENCE: 34

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 35
<211> LENGTH: 32
<212> TYPE: PRT
<213> ORGANISM: Human papillomavirus type 16

<400> SEQUENCE: 35

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

<210> SEQ ID NO 36
<211> LENGTH: 35
<212> TYPE: PRT
<213> ORGANISM: Human papillomavirus type 16

<400> SEQUENCE: 36

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35

<210> SEQ ID NO 37
<211> LENGTH: 35
<212> TYPE: PRT
<213> ORGANISM: Human papillomavirus type 16

<400> SEQUENCE: 37

Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35

<210> SEQ ID NO 38
<211> LENGTH: 35
<212> TYPE: PRT
<213> ORGANISM: Human papillomavirus type 16

<400> SEQUENCE: 38

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 39
<211> LENGTH: 35
<212> TYPE: PRT
<213> ORGANISM: Human papillomavirus type 16

```
<400> SEQUENCE: 39

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35
```

HPV EPITOPES TARGETED BY T CELLS INFILTRATING CERVICAL MALIGNANCIES FOR USE IN VACCINES

CROSS-REFERENCE TO RELATED APPLICATIONS

This application is a Continuation of U.S. patent application Ser. No. 16/287,559 filed Feb. 27, 2019, which is a Continuation Application of U.S. patent application Ser. No. 15/678,970, filed Aug. 16, 2017, which is a Continuation Application of U.S. patent application Ser. No. 14/453,286, filed Aug. 6, 2014, now a U.S. Pat. No. 9,764,023, which is a Continuation Application of U.S. patent application Ser. No. 12/592,528, filed Feb. 16, 2010, which is a Continuation Application of International Patent Application No. PCT/NL2008/050320, filed May 27, 2008, which claims priority to European Patent Application No. 07109281.1, filed May 31, 2007, and European Patent Office Application No. 07109287.8, filed May 31, 2007, and claims the benefit of U.S. Provisional Patent Application No. 61/941,070, filed May 31, 2007, the entirety of these applications are herein incorporated by reference in their entirety.

SEQUENCE LISTING

The instant application contains a Sequence Listing which is being submitted electronically in ASCII format and is hereby incorporated by reference in its entirety. Said ASCII copy, created on Mar. 31, 2020, is named 069818-0364_SL.txt and is 15,272 bytes in size.

FIELD OF THE INVENTION

The present invention relates to the fields of medicine and immunology. In particular it relates to novel HPV epitopes that may be used in the prevention, therapy and/or diagnosis of HPV associated diseases.

BACKGROUND OF THE INVENTION

Cervical cancer is the second most common cancer worldwide (Bosch et al. 2003). High risk human papilloma virus (HPV) type 16 and 18 are the cause of cervical cancer in around two third of all patients (Bosch et al. 1995, Munoz et al. 2003). The HPV genome encodes two oncoproteins, E6 and E7, which are constitutively expressed in high grade cervical lesions and cancer because they are required for the onset and maintenance of the malignant cellular phenotype (Zur Hausen, 1996).

The tumor-specific expression of these oncoproteins as well as the presence of low levels of circulating E6- and E7-specific T cells detected in the peripheral blood of almost half of patients with cervical cancer (de Jong et al. 2004, van der Berg et al. 2001, Welters et al. 2003, Welters et al. 2006, Ressing et al. 1996, Bontkes et al. 2000, Luxton et al. 1996) suggested that they could serve as tumor rejection antigens. However, the existence of circulating HPV-specific T cells does not imply that they contribute to the anti-tumor response. In order to control the disease, these T cells should at least be able to home to the tumor sites. Indeed, a proportion of cervical carcinomas are infiltrated by lymphocytes (Bethwaite et al. 1996, Chao et al. 1999, Piersma et al. 2007) but in-depth knowledge on the specificity and type of the T cells infiltrating these cervical tumors is still lacking, probably due to the relative difficulties to establish T cell cultures from tumor tissue. Nonetheless, a few early pioneers were able to isolate HPV-specific tumor infiltrating lymphocytes (TIL) from tumors, resulting in the identification of two single CD8$^+$ T cell epitopes of HPV16 (Evans et al. 1997, Oerke et al. 2005) and two CD4 T cell epitopes specific for the less prevalent high risk subtypes HPV59 and HPV33 (Hohn et al. 1999, Hohn et al. 2000). However, larger studies on cervical tissue-infiltrating lymphocytes are urgently needed to comprehend the contribution and role of the HPV-specific adaptive immune response in cervical cancer. In addition, this will allow the rational design of successful immune intervention strategies.

Recent studies showed that two cytokines, IL-7 and IL-15, have a major role in the expansion and survival of CD4$^+$ and CD8$^+$ effector memory T cells. IL-7 provides survival signals for effector T cells (Li et al. 2003). IL-15 is a critical growth factor in initiating T cell divisions, and in contrast to IL-2—which is generally used to expand TIL cultures—does not limit continued T-cell expansion (Li et al. 2001). Furthermore, IL-15 can also act as an antigen-independent activator of CD8($^+$) memory T cells (Liu et al. 2002). Together, IL-7 and IL-15 can expand with very high efficiency effector memory T cells, while central memory T cells are less responsive and naive T cells fail to respond to stimulation with these cytokines (Geginat et al. 2001, McKinlay et al. 2007, Bacchetta et al. 2002).

A number of previous studies have reported MHC class II restricted recognition of synthetic peptides consisting of sequences from in HPV16 E6 and/or E7 proteins by T cell from peripheral blood mononuclear cells (PBMC).

WO 02/070006 discloses a DR1 restricted response against a peptide consisting of amino acids 127-142 of HPV16 E6 protein, a DQ2 restricted response against a peptide consisting of amino acids 35-50 of HPV16 E7 protein, a DR3 restricted response against a peptide consisting of amino acids 43-77 of HPV16 E7 protein and a DR15 restricted response against a peptide consisting of amino acids 50-62 of HPV16 E7 protein.

Strang et al. disclose a DR7 restricted response in PBMC from asymptomatic individuals against a synthetic peptide consisting of amino acids 42-57 of HPV16 E6 protein.

Altmann et al. discloses a response in PBMC from asymptomatic individuals that are DR1/DR11-typed against a synthetic peptide consisting of amino acids 5-18 of HPV16 E7 protein, a response in PBMC from asymptomatic individuals that are DR4/DR13-typed against a synthetic peptide consisting of amino acids 17-34 of HPV16 E7 protein and a response in PBMC from asymptomatic individuals that are DR4/DR13-typed against a synthetic peptide consisting of amino acids 69-82 of HPV16 E7 protein.

WO 02/090382 discloses the binding affinities for a series of overlapping peptides from HPV16 E6 and E7 proteins for HLA-DR molecules that are most prevalent in the caucasian population. WO 02/090382 further reports responses against a number of the HPV16 E6 and E7 peptides in CD8-depleted PBMC from patients with bowenoid papulosis.

There is however still a need for knowledge about the presence, type and specificity of tumor infiltrating lymphocytes in HPV-associated malignancies, preferably for the more prevalent high risk subtypes such as HPV16, 18, 31, 33 and 45. It is an object of the present invention to provide for HPV epitopes that are targets for tumor infiltrating lymphocytes and that may be used in the prevention, therapy and/or diagnosis of HPV associated diseases.

DESCRIPTION OF THE INVENTION

The present invention provides novel T cell epitopes that are identified on the basis of our analysis of the presence and HPV16 or HPV18 specificity of cervix infiltrating T cells in a large group of 70 patients with cervical malignancies. We found that these infiltrating lymphocytes comprise HPV-specific T cells. In more detailed analysis we identified 17 novel CD4+ and CD8+ T cell epitopes and their HLA-restriction elements but also revealed that HPV-specific immune response directed towards all parts of the E6 and E7 oncoproteins. Unexpectedly, the vast majority of the CD4+ T cell epitopes were presented in the context of the less abundantly expressed HLA-DQ and HLA-DP molecules. Since the identified T cell epitopes constitute physiological targets in the immune response to HPV16 and HPV18 positive tumors they are valuable targets for optimization of prevention against HPV-related diseases and immunotherapy in patients with HPV related diseases.

In one aspect, the present invention thus relates to amino acid sequences of newly identified CD4+ Th and CD8+ CTL cell epitopes of HPV, as well as HPV derived synthetic peptides and immunogenic compositions comprising these are also part of the present invention. Such peptides result in a much improved, enhanced and prolonged CD8+ CTL effector and memory response upon administration in a wide range of patients with HPV associated disease, including HPV related malignancies. Such peptides can also induce a much improved pro-inflammatory microenvironment that is more likely to be infiltrated by effector cells, as the result of this CD4+ Th response.

Since the peptides of the invention are preferably used as a vaccine alone or in combination or as part of an immunogenic composition, the peptides are preferably named vaccine peptides and the composition vaccine compositions.

The use of relatively short peptides is highly preferred for medical purposes as these can be synthesized in vitro efficiently, which is not possible or uneconomical for native proteins larger than about 100 amino acids. Chemical synthesis of peptides is routine practice and various suitable methods are known to the skilled person. Chemical synthesis of peptides also overcomes the problems associated with recombinant production of intact proteins, which is difficult to standardize and requires extensive purification and quality control measures. Peptides with a length that exceeds the length of HLA class I and class II epitopes (e.g. having a length as indicated below herein) are particularly advantageous for use as vaccine component because they are large enough to be taken up by professional antigen presenting cells, in particular DC, as explained in WO02/070006 and processed in the DC before cell surface presentation of the contained HLA class I and class II epitopes takes place. Therefore, the disadvantageous induction of T cell tolerance by the systemic presentation of minimal HLA class I epitopes on non-antigen presenting cells (as shown in Toes et al., 1996, Proc. Natl. Acad. Sci. U.S.A 93:7855 and Toes et al., 1996, J. Immunol. 156:3911), is prevented by the application of peptides of the invention having a length as indicated herein (as shown in Zwaveling et al., 2002, J. Immunol. 169:350). Peptides comprising epitopes which are to be presented to T cell receptors of CTL and/or Th cells preferably have sufficient length to contain both HLA class I and HLA class II epitopes In a first aspect of the invention there is provided a peptide comprising a contiguous amino acid sequence selected from the full length amino acid sequences of at least one of the HPV E6 and E7 proteins. Preferably, the contiguous amino acid sequence selected from the full length amino acid sequences of the HPV E6 and E7 proteins from a high risk HPV serotype, such as serotypes 16, 18, 31, 33 or 45, more preferably from the amino acid sequences of the HPV E6 and E7 serotypes 16, 18, 31 or 33, most preferably from serotypes 16 or 18, of which 16 is most preferred. The amino acid sequence of the HPV serotype 16 E6 and E7 proteins are depicted in SEQ ID No. 1 and 2, respectively. The amino acid sequence of the HPV serotype 18 E6 and E7 proteins are depicted in SEQ ID No. 3 and 4, respectively.

Preferably, the peptide comprises at least one HLA class II Th cell epitope and/or at least one HLA class I cytotoxic T cell epitope, preferably an epitope as herein defined below in more detail. Preferably the peptide has a length of no more than 100 amino acids and comprises at least 19 contiguous amino acids selected from the amino acid sequence of one of the above-defined HPV proteins, wherein the peptide preferably comprises at least one of an HLA class II epitope and an HLA class I epitope, more preferably both at least one HLA class II epitope and at least one HLA class I epitope and most preferably (but not necessarily) both from the amino acid sequence of one of the above-defined HPV proteins. More preferably, in the peptide at least one HLA class II epitope and at least one HLA class I epitope are present within a contiguous amino sequence from the amino acid sequence of one of the above-defined HPV proteins. For the sake of clarity, the peptides of the invention preferably comprise HLA class I presented epitopes and/or HLA class II presented epitopes. Each of these epitopes are presentable and will bind to the corresponding specific HLA molecule present on the cells after having been processed as described herein. In the context of the invention, an HLA-haplotype specific epitope may therefore also be referred to as an epitope binding to, presented by and/or being restricted by that HLA-haplotype.

Within the context of the invention, "a peptide has a length of no more than 100 amino acids" preferably means that the number of consecutive amino acids originating from a HPV protein and present in a peptide as defined herein, is 100, 98, 96, 94, 92, 90 or less. Therefore, by definition, a peptide as defined herein is distinct from a full length HPV protein. Such a peptide may comprise additional amino acids than the ones originating from a HPV protein or may entirely be made of or consist of an amino acid sequence originating from a HPV protein. The length of the contiguous amino acid sequence from one of the above-defined HPV proteins comprised within the peptide, preferably is at least 19, 20, 21, 22, 23, 24, 25, 26, 27, 28, 29, 30, 31, 32, 33, 34, 35, 36, 37, 38, 39, 40, 41, 42, 43, 44 or 45 amino acids and/or preferably no more than 100, 99, 98, 97, 96, 95, 94, 93, 92, 91, 90, 89, 88, 87, 86, 85, 84, 83, 82, 81, 80, 60, 50, 45, 40, 35, 33 or 30 amino acids, more preferably the length of the contiguous amino acid sequence from one of the above-defined HPV proteins comprised within the peptide is 19-45, even more preferably 22-40 amino acids, even more preferably 30-35 and most preferably 33-35 amino acids. In another preferred embodiment, the peptide of the invention consists of any of the contiguous amino acid sequence from the HPV proteins as defined herein, whereby it is understood that no amino acids are appended to either end of the contiguous amino acid sequence from the HPV protein that are not contiguous with this amino acid sequence in the sequence of the native HPV protein. The peptides of the invention may be easily synthesized and are large enough to be taken up by professional antigen presenting cells, processed by the proteasome and have sufficient physical capacity and length to contain at least one HLA class I and/or at least one HLA class II epitope. Optionally a peptide may comprise N- or C-terminal extensions, which may be amino acids, modified amino acids or other functional groups that may for instance enhance bio-availability, cellular uptake, processing and/or solubility.

A preferred peptide of the invention has a length of no more than 100, 98, 96, 94, 92 amino acids and comprises at least 19 contiguous amino acids from the amino acid sequence of at least one of an HPV E6 and E7 protein, wherein the contiguous amino acid sequence comprises an epitope that is recognized by a T cell that infiltrates a cervical neoplastic lesion or by a T cell that is present in or isolated from a lymph node from the pelvic region, that is draining from the cervical neoplastic lesion, preferably a T cell that is present in or isolated from a draining lymph node comprising metastatic tumor cells. A peptide according to the invention is preferably used to induce a T-cell response.

In a further preferred peptide of the invention the contiguous amino acid sequence comprises an epitope that is selected from the group consisting of amino acids 11-32 of an HPV E6 protein, amino acids 37-68 of an HPV E6 protein, amino acids 52-61 of an HPV E6 protein, amino acids 51-72 of an HPV6 protein, amino acids 55-86 of an HPV E6 protein, amino acids 61-82 of an HPV E6 protein, amino acids 71-92 of an HPV E6 protein, amino acids 73-105 of an HPV E6 protein, amino acids 91-112 of an HPV E6 protein, amino acids 101-122 of an HPV E6 protein, amino acids 121-142 of an HPV E6 protein, amino acids 129-138 of an HPV E6 protein, amino acids 1-32 of an HPV E7 protein, amino acids 21-42 of an HPV E7 protein, amino acids 51-72 of an HPV E7 protein, amino acids 76-86 of an HPV E7 protein; amino acids 13-22 of an HPV E6 protein, amino acids 29-38 of an HPV E6 protein, amino acids 52-61 of an HPV E6 protein, amino acids 129-138 of an HPV E6 protein, amino acids 137-146 of an HPV E6 protein, amino acids 149-158 of an HPV E6 protein, and amino acids 11-19 of an HPV E7 protein. In yet a further preferred peptide of the invention the contiguous amino acid sequence comprises an epitope that is selected from the group consisting of SEQ ID No.'s 5-26.

A preferred peptide of the invention comprises at least an HPV-specific class II CD4+ Th cell epitope. Preferably, a class II CD4+ Th cell epitope comprised in a peptide according to the invention is capable of inducing or activating a CD4+ Th cell in human patient with an HPV associated disease and/or a healthy control. The activation is preferably assessed ex vivo or in vivo, more preferably in a human patient with an HPV associated disease, such as an HPV associated malignancy, whose infected and/or tumor cells express an HPV protein as defined above. Most preferably, the HLA class II epitope is capable of activating a CD4+ Th memory and/or CD4+Th-effector response, i.e. activation of a CD45RO-positive CD4+ Th cell. This will lead, by virtue of the 'license to kill' signal through CD40-triggering of DC (Lanzavecchia, 1998) to a more robust CD8+ effector and memory CTL response. In another setting the activated CD4+Th-cells may activate non-HLA restricted killer cells of the immune system.

A preferred class II CD4+ Th cell epitope comprised in (a contiguous sequence in) a peptide according to the invention is selected from the group consisting of amino acids 11-32 of an HPV E6 protein, amino acids 37-68 of an HPV E6 protein, amino acids 52-61 of an HPV E6 protein, amino acids 51-72 of an HPV E6 protein, amino acids 55-86 of an HPV E6 protein, amino acids 61-82 of an HPV E6 protein, amino acids 71-92 of an HPV E6 protein, amino acids 73-105 of an HPV E6 protein, amino acids 91-112 of an HPV E6 protein, amino acids 101-122 of an HPV E6 protein, amino acids 121-142 of an HPV E6 protein, amino acids 129-138 of an HPV E6 protein, amino acids 1-32 of an HPV E7 protein, amino acids 21-42 of an HPV E7 protein, amino acids 51-72 of an HPV E7 protein, and amino acids 76-86 of an HPV E7 protein. A more preferred class II CD4+ Th cell epitope comprised in (a contiguous sequence in) a peptide according to the invention is selected from the group consisting SEQ ID No.'s 5-21.

Another preferred class II CD4+ Th cell epitope comprised in (a contiguous sequence in) a peptide according to the invention is an epitope that is restricted by a haplotype selected from the group consisting of DR4, DR7, DR12, DR15, DP1, DP0201, DP4, DP14, DP1401, DP17, DQ5, DQ6, DP1901, DQ*0301, DQ*0302, DQ*0308, DQ*0501. A further preferred class II CD4+ Th cell epitope comprised in (a contiguous sequence in) a peptide according to the invention is an epitope that is restricted by a DP or DQ haplotype, of which DP1, DP0201, DP4, DP14, DP1401, DP17, DQ5, DQ6, DP1901, DQ*0301, DQ*0302, DQ*0308, and DQ*0501 are more preferred. One previously disclosed HLA-DQ restricted epitope (WO02/070006) consists of amino acid 35-50 of the HPV16 E7 protein. This epitope is however recognized epitope by peripheral T cells and not by a T cell that infiltrates a cervical neoplastic lesion or by a T cell that is present in or isolated from a lymph node from the pelvic region, that is draining from the cervical neoplastic lesion. The contiguous sequence in a peptide of the invention therefore preferably does not comprise an epitope consisting of amino acid 35-50 of the HPV16 E7 protein. Thus, a preferred class II CD4+ Th cell epitope comprised in (a contiguous sequence in) a peptide according to the invention is an epitope that is restricted by a DP or DQ haplotype and not by a DR haplotype. Expression of HLA-DR molecules is known to be upregulated on tumor cells. Presentation in that context may, as presentation of antigens on non-professional Antigen Presenting Cells (APC), lead to induction of tolerance. Expression of HLA-DP or -DQ molecules is much lower but HLA-DQ and HLA-DP epitopes when presented on professional APC, such as e.g. DC, may nonetheless lead to effective immune responses.

Yet another preferred class II CD4+ Th cell epitope comprised in (a contiguous sequence in) a peptide according to the invention is an epitope that is restricted by a DP or DQ haplotype and that is an epitope of an HPV E6 or E7 protein, more preferably an E6 or E7 protein of HPV serotypes 16, 18, 31, 33 or 45, and most preferably of HPV serotypes 16 or 18, of which 16 is most preferred.

Yet a further preferred class II CD4+ Th cell epitope comprised in (a contiguous sequence in) a peptide according to the invention is an epitope selected from the group consisting of amino acids 11-32 of an HPV E6 protein, amino acids 37-68 of an HPV E6 protein, amino acids 52-61 of an HPV E6 protein, amino acids 51-72 of an HPV E6 protein, amino acids 61-82 of an HPV E6 protein, amino acids 71-92 of an HPV E6 protein, amino acids 73-105 of an HPV E6 protein, amino acids 91-112 of an HPV E6 protein, amino acids 101-122 of an HPV E6 protein, amino acids 121-142 of an HPV E6 protein, amino acids 1-32 of an HPV E7 protein, and amino acids 51-72 of an HPV E7 protein. A more preferred class II CD4+ Th cell epitope comprised in (a contiguous sequence in) a peptide according to the invention is selected from the group consisting SEQ ID No.'s 5, 6, 7, 9, 10, 11, 12, 13, 16, 18, 19, 20 and 21.

In another preferred embodiment, a peptide of the invention comprises at least an HPV-specific class I CD8+ CTL epitope. In addition, said HLA class I epitope is preferably capable of activating a CD8+ CTL response. Most preferably, the CTL activating capability has been demonstrated ex vivo and/or in vivo, in human healthy control individuals or even more preferably in a human patient with an HPV associated disease, such as an HPV associated malignancy, whose infected and/or tumor cells express an HPV protein as defined above. The presence of both an HLA class I and a class II epitope within one peptide has been observed to be particularly advantageous due to synergy in mounting and maintaining an effective CTL cell response (as shown in Zwaveling et al., 2002).

Peptides comprising epitopes which are to be presented to T cell receptors of CTL and/or Th cells preferably fulfill a number of requirements. The peptides preferably have sufficient length to contain both HLA class I and HLA class II epitopes. Furthermore, the peptides preferably comprise anchor residues within their HLA class I binding parts to enable binding to the class I molecules, respectively. The stability of the interaction between peptide and presenting MHC molecule preferably is sufficient in order to generate a significant and effective immune response. In the context of the present invention, the stability of the interaction between peptide and presenting MEW molecule therefore preferably is such that the peptide has an intermediate to high affinity binding, whereby an $IC_{50} \leq$ about 5 µM is considered high affinity binding, about 5 µM<$IC_{50} \leq$ about 15 µM is considered intermediate affinity binding, about 15 µM<$IC_{50} \leq$ 100 µM is judged low affinity binding and $IC_{50}$>about 100 µM was regarded as no binding, whereby the binding affinity of a peptide for an MHC molecule is determined as described in van der Burg et al., 1995 and Kessler et al., 2003.

A specific proteasomal cleavage site generating the C-terminus of the epitope, preferably is present exactly after the epitope amino acid sequence in order to be liberated from the larger peptide and presented on the HLA class I molecule. Length requirements are much less strict for HLA class II presented epitopes, therefore a need for precise enzymatic generation of the class II binding peptide is less absolute. These requirements have been used in the present invention to localize and design peptides in the full length sequences of HPV proteins, particularly in the HPV E6 and E7 proteins, which comprise preferred CTL and Th cell epitopes and/or combinations thereof and are thus highly suitable peptides for vaccination purposes.

Moreover, in vitro and ex vivo T cell experiments are preferably used to confirm the capability of peptides according to the invention to induce substantial CD4$^+$ Th and CD8$^+$ CTL responses. The peptides of the present invention thereby provide a marked improvement in the selection of relatively short peptides that may be chemically synthesized, comprising the most potent and most widely applicable HLA class I and/or class II presented T cell epitopes derived from the HPV E6 and E7 tumor antigens. The peptides are particularly optimized with respect to their proteasomal cleavage and preferably contain at least one of HLA class I and class II epitopes and more preferably both HLA class I and class II epitopes. The liberation of the C-termini of CTL epitopes contained within the peptides of the invention by the 20S proteasome provides HLA class I binding fragments with CD8$^+$ CTL stimulatory capacity.

The HLA class I epitopes in the HPV peptides of the invention are preferably capable of being presented on HLA alleles that are predominant in the population of human subjects to be treated. Preferred HLA class I epitopes in HPV derived peptides of the invention are epitopes capable of binding to HLA-A2, HLA-B7, HLA-B14, HLA-B27, HLA-B57, and HLA*0201. The most preferred HLA class I CTL epitopes are the HLA-B binding HPV epitopes, of which HLA-B7, HLA-B14, HLA-B27, HLA-B57 are most preferred. The HLA class I epitope preferably has a high peptide binding capacity ($IC_{50}$<about 5 µM peptide) or at least intermediate affinity (5 µM<$IC_{50}$<about 15 µM peptide). A preferred class I CTL epitope comprised in (a contiguous sequence in) a peptide according to the invention is an epitope that is restricted by class I haplotype as indicated above and that is an epitope of an HPV E6 or E7 protein, more preferably an E6 or E7 protein of HPV serotypes 16, 18, 31, 33 or 45, and most preferably of HPV serotypes 16 or 18, of which 16 is most preferred.

A preferred class I CTL epitope comprised in (a contiguous sequence in) a peptide according to the invention is selected from the group consisting of amino acids 13-22 of an HPV E6 protein, amino acids 29-38 of an HPV E6 protein, amino acids 52-61 of an HPV E6 protein, amino acids 129-138 of an HPV E6 protein, amino acids 137-146 of an HPV E6 protein, amino acids 149-158 of an HPV E6 protein and amino acids 11-19 of an HPV E7 protein. A more preferred class II CD4$^+$ Th cell epitope comprised in (a contiguous sequence in) a peptide according to the invention is selected from the group consisting SEQ ID No.'s 7, 14, 22-26.

A preferred epitope comprised in a peptide according to the invention is an epitope that is presented by an HLA-B molecule. Preferably, the HLA-B molecule is an HLA-B7, HLA-B14, HLA-B27 or HLA-B57 molecule. Such epitope is selected from the group consisting of SEQ ID No.'s 7, 22, 24, 25 and 26.

Another preferred epitope comprised in a peptide according to the invention is an epitope that is presented by an HLA-A molecule. Preferably the HLA-A molecule is an HLA-A2, or HLA*0201 molecule. Such epitope is selected from the group consisting of SEQ ID No.'s 23 and 26.

According to a more preferred embodiment, peptides of the invention have a length of no more than 100, 98, 96, 94, 94, 92 amino acids and comprise a contiguous amino acid sequence from an HPV protein selected from the group consisting of amino acids 1-32 of an HPV E6 protein (SEQ ID NO: 27), amino acids 19-50 of an HPV E6 protein (SEQ ID NO: 28), amino acids 41-65 of an HPV E6 protein (SEQ ID NO: 29), amino acids 55-80 of an HPV E6 protein (SEQ ID NO: 30), amino acids 71-95 of an HPV E6 protein (SEQ ID NO: 31), amino acids 85-109 of an HPV E6 protein (SEQ ID NO: 32), amino acids 91-122 of an HPV E6 protein (SEQ ID NO: 33), amino acids 109-140 of an HPV E6 protein E6 (SEQ ID NO: 34), amino acids 127-158 of an HPV E6 protein (SEQ ID NO: 35), amino acids 1-35 of an HPV E7 protein (SEQ ID NO: 36), amino acids 22-56 of an HPV E7 protein (SEQ ID NO: 37), amino acids 43-77 of an HPV E7 protein (SEQ ID NO: 38), and amino acids 64-98 of an HPV E7 protein (SEQ ID NO: 39). More preferably the peptides of the invention consist of a contiguous amino acid sequence from an HPV protein selected from the group consisting of amino acids 1-32 of an HPV E6 protein (SEQ ID NO: 27), amino acids 19-50 of an HPV E6 protein (SEQ ID NO: 28), amino acids 41-65 of an HPV E6 protein (SEQ ID NO: 29), amino acids 55-80 of an HPV E6 protein (SEQ ID NO: 30), amino acids 71-95 of an HPV E6 protein (SEQ ID NO: 31), amino acids 85-109 of an HPV E6 protein (SEQ ID NO: 32), amino acids 91-122 of an HPV E6 protein (SEQ ID NO: 33), amino acids 109-140 of an HPV E6 protein E6 (SEQ ID NO: 34), amino acids 127-158 of an HPV E6 protein (SEQ ID NO: 35), amino acids 1-35 of an HPV E7 protein (SEQ ID NO: 36), amino acids 22-56 of an HPV E7 protein (SEQ ID NO: 37), amino acids 43-77 of an HPV E7 protein (SEQ ID NO: 38), and amino acids 64-98 of an HPV E7 protein (SEQ ID NO: 39). The contiguous amino acid sequence from the HPV E6 or E7 proteins are preferably of HPV serotypes 16, 18, 31, 33 or 45, and most preferably of HPV serotypes 16 or 18, of which 16 is most preferred.

It is clear to a skilled person that a peptide as defined herein will have a desired and advantageous property linked to the presence of an epitope in said peptide (for example an epitope which is identified in the invention as being presented by at least one of an HLA-DQ and HLA-DP molecule and/or as being recognized by a T cell that infiltrates a cervical neoplastic lesion or by a T cell from a draining lymph node) as soon as this epitope is present in said peptide. A peptide according to the invention is preferably used to induce a T-cell response. The skilled person will understand that even if this application does not identify each peptide that can be designed as comprising or consisting of a desired epitope as identified herein, nevertheless the invention encompasses any peptide as defined herein comprising or consisting of an epitope as identified herein. In a preferred embodiment, a peptide is distinct from a HPV protein. In another preferred embodiment, a peptide does not comprise or consist of amino acid 35-50 of the HPV16 E7.

For example, one preferred epitope is SEQ ID NO:5 (aa 11-32 of HPV16 E6). This paragraph is illustrative and may be applied for each epitope as identified herein. Any peptide comprising SEQ ID NO:5 is encompassed by the present invention and may be used according to the present invention. In this preferred embodiment, a peptide is distinct from a HPV protein. Preferred amino acid length for a peptide of the invention has already been defined herein. When designing a peptide of the invention, a peptide may start at the N-terminal site of a given epitope as identified herein or end at the C-terminal site of a given epitope as identified herein. Alternatively, a given epitope (for example SEQ ID NO:5) may be comprised within a peptide of the invention. Using SEQ ID NO:5 as example, if we design a peptide having a length of 45 amino acids, such peptide may consist or comprise 11-56, 1-45, 2-46, 3-47, 4-48, 5-49, 5-50 from HPV16 E6. A peptide of the invention may further comprise any other HPV epitope as defined herein or as already known to the skilled person.

In this preferred embodiment (SEQ ID NO:5 as epitope), a peptide does not comprise or consist of amino acid 9-33 of the HPV16 E6 as disclosed in US2005/0142541. In this preferred embodiment, a peptide does not comprise or consist of amino acid 1-37 of the HPV16 E6 as disclosed in EP 451 550. In this preferred embodiment, a peptide does not comprise or consist of amino acid 8-37 of the HPV16 E6 as disclosed in U.S. Pat. No. 5,629,161. In a preferred embodiment, a peptide comprising SEQ ID NO:5 consists of or comprises 10-32, 1-32, 1-45, 11-56, 2-46, 3-47, 4-48, 5-49, 5-50 the numbers indicating the starting and ending amino acid from HPV16 E6

In another preferred embodiment (SEQ ID NO:8 as epitope, aa 55-86 from HPV16 E6), a peptide does not comprise or consist of a fragment of HPV16 E6 as disclosed on uniprot having the following accession number Q919B2 (1-99, numbers indicating the starting and ending amino acid from HPV16 E6) or Q80882 (1-84). For this embodiment also, a peptide comprising SEQ ID NO:8 may start at the N-terminal site of this epitope, or end at the C-terminal site of this epitope, or this epitope may be present within the peptide. For example if we design a peptide having a length of 45 amino acids, such peptides may consist or comprise 55-100, 41-86, 45-90. In a preferred embodiment, a peptide comprising SEQ ID NO:8 consists of or comprises 55-100, 41-86, 45-90, the numbers indicating the starting and ending amino acid in the HPV16 E6 protein amino acid sequence.

The HPV-derived peptides of the invention may be modified by deletion or substitution of one or more amino acids, by extension at the N- and/or C-terminus with additional amino acids or functional groups, which may improve bio-availability, targeting to T-cells, or comprise or release immune modulating substances that provide adjuvant or (co)stimulatory functions. The optional additional amino acids at the N- and/or C-terminus are preferably not present in the corresponding positions in the native amino acid sequence of the HPV protein, more preferably they are not from any of the HPV E6 or E7 amino acid sequences (e.g. SEQ ID No.'s 1-4). The skilled person will appreciate that HPV amino acid sequences of the various HPV serotypes are expressly included in the invention.

The HPV-derived peptides of the invention are obtainable by chemical synthesis and subsequent purification (e.g. see Example 1). The HPV-derived peptides of the invention are preferably soluble in physiologically acceptable watery solutions (e.g. PBS) comprising no more than 35, 20, 10, 5 or 0% DMSO. In such a solution the peptides are preferably soluble at a concentration of at least 0.5, 1, 2, 4, or 8 mg peptide per ml. More preferably, a mixture of more than one different HPV-derived peptides of the invention is soluble at a concentration of at least 0.5, 1, 2, 4, or 8 mg peptide per ml in such solutions.

A preferred use of the peptides according to the invention is their use as a medicament, whereby more preferably the peptides are used as a vaccine or an active component thereof. Each peptide may be either used alone or preferably in combinations of at least 2, 3, 4, 5, 6, 7, 8, 9, 10, 12, 13, 15 and up to 20 different peptides of the invention, in the treatment and/or prevention of cancer, for the manufacture of medicaments, preferably vaccine for the treatment or prevention of an HPV associated disease. Such a medicament and/or anti-tumor vaccine according to the invention may be used to treat patients suffering from or at risk of developing the following, non extensive list of cervical intraepithelial neoplasia of the cervix (CIN), vulva (VIN), vagina (VaIN), anus (AIN), and penis (PIN), as well as cancer of the cervix, vulva, vagina, anus, penis, and head & neck.

In a further aspect, the current invention further relates to compositions which may be useful for treatment and/or vaccination of human subjects, comprising at least at least 2, 3, 4, 5, 6, 7, 8, 9, 10, 12, 13, 15 and up to 20 different peptides of the invention as defined above and optionally one or more pharmaceutically acceptable excipients, in particular adjuvants and immune modulators. Preferably, the composition is a pharmaceutical composition and/or intended for use as a medicament. The pharmaceutical composition is preferably intended for vaccination. The pharmaceutical composition are preferably used for the treatment and/or prevention of cancer, for the manufacture of medicaments, preferably vaccine for the treatment or prevention of an HPV associated disease. A non-exhaustive list of an HPV associated diseases has already been given herein.

Thus, in one aspect the invention relates to the use of a peptide for the manufacture of a medicament for the prevention and/or treatment of an HPV associated disease, wherein the peptide has a length of no more than 100, 98, 96, 94, 92 amino acids and comprises at least 19 contiguous amino acids from the amino acid sequence of at least one of an HPV E6 and E7 protein, wherein the contiguous amino acid sequence comprises an epitope that is presented by at least one of an HLA-DQ and HLA-DP molecule. Preferably, the epitope is not the epitope presented in the context of HLA-DQ2 and consisting of amino acid 35-50 of the HPV16 E7 protein. Alternatively or in combination with previous preferred embodiment in another preferred embodiment, the contiguous amino acid sequence comprises an epitope that is recognized by a T cell that infiltrates a cervical neoplastic lesion or by a T cell from a draining lymph node. The peptides, contiguous amino acid sequences and epitopes are preferably as defined herein above.

In another aspect the invention relates to the use of a peptide for the manufacture of a medicament for the prevention and/or treatment of an HPV related disease, wherein the peptide has a length of no more than 100, 98, 96, 94, 92, amino acids and comprises at least 19 contiguous amino acids from the amino acid sequence of at least one of an HPV E6 and E7 protein, wherein the contiguous amino acid sequence comprises an epitope that is recognized by a T cell that infiltrates a cervical neoplastic lesion or by a T cell from a draining lymph node. The peptides, contiguous amino acid sequences and epitopes are preferably as defined herein above.

Formulation of medicaments, ways of administration and the use of pharmaceutically acceptable excipients are known and customary in the art and for instance described in Remington; The Science and Practice of Pharmacy, $21^{st}$ Edition 2005, University of Sciences in Philadelphia. Pharmaceutical compositions and medicaments of the invention are preferably formulated to be suitable for intravenous or subcutaneous, or intramuscular administration, although other administration routes can be envisaged, such as mucosal administration or intradermal and/or intracutaneous administration, e.g. by injection. Intradermal administration is preferred herein. Advantages and/or preferred embodiments that are specifically associated with intradermal administration are later on defined in a separate section entitled "intradermal administration".

It is furthermore encompassed by the present invention that the administration of at least one peptide and/or at least one composition of the invention may be carried out as a single administration. Alternatively, the administration of at least one peptide and/or at least one composition may be repeated if needed and/or distinct peptides and/or compositions of the invention may be sequentially administered.

The pharmaceutically compositions (also referred to as medicaments) according to the invention may preferably comprise at least one immune response stimulating compound or adjuvant. Advantageously the pharmaceutical composition according to the invention may additionally comprise one or more synthetic adjuvants. These adjuvants may be admixed to the pharmaceutical composition according to the invention or may be administered separately to the mammal or human to be treated. Particularly preferred are those adjuvants that are known to act via the Toll-like receptors and/or via a RIG-1 (Retinoic acid-Inducible Gene-1) protein and/or via an endothelin receptor. Immune modifying compounds that are capable of activation of the innate immune system can be activated particularly well via Toll like receptors (TLR's), including TLR's 1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heat shock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *Streptococcus* heat labile soluble factor (GBS-F) or *Staphylococcus* modulins. TLR7 may be activated by imidazoquinolines. TLR9 may be activated by unmethylated CpG DNA or chromatin—IgG complexes. In particular TLR3, TLR7 and TLR9 play an important role in mediating an innate immune response against viral infections, and compounds capable of activating these receptors are particularly preferred for use in the methods of treatment and in the compositions or medicaments according to the invention. Particularly preferred adjuvants comprise, but are not limited to, synthetically produced compounds comprising dsRNA, poly(I:C), unmethylated CpG DNA which trigger TLR3 and TLR9 receptors, IC31, a TLR 9 agonist, IMSAVAC, a TLR 4 agonist, Montanide ISA-51, Montanide ISA 720 (an adjuvant produced by Seppic 7, France). RIG-1 protein is known to be activated by ds-RNA just like TLR3 (Immunity, (2005), 1:19-28). In another preferred embodiment, the synthetic adjuvant compounds are physically linked to the peptides of the invention. Physical linkage of adjuvants and costimulatory compounds or functional groups, to the HLA class I and HLA class II epitope comprising peptides provides an enhanced immune response by simultaneous stimulation of antigen presenting cells, in particular dendritic cells, that internalize, metabolize and display antigen. Another preferred immune modifying compound is an inhibitor of an endothelin receptor such as BQ-788 (Buckanovich R J et al. Nature Medicine (2008), 14:28-36, Ishikawa K, PNAS (1994) 91:4892). BQ-788 is N-cis-2,6-dimethylpiperidinocarbonyl-L-gamma-methylleucyl-D-1-methoxycarbonyltryptophanyl-D-norleucine. However any derivative of BQ-788 or modified BQ-788 compound is also encompassed within the scope of this invention.

Furthermore, the use of antigen presenting cell (co)stimulatory molecules, as set out in WO99/61065 and in WO03/084999, in combination with the peptides and compositions of the invention is preferred. In particular the use of 4-1-BB and/or CD40 ligands, agonistic antibodies, OX40 ligands or functional fragments and derivates thereof, as well as synthetic compounds with similar agonistic activity are preferably administered separately or combined with the peptides of the invention to subjects to be treated in order to further stimulate the mounting of an optimal immune response in the subject.

In addition a preferred embodiment comprises delivery of the peptides, with or without additional immune stimulants such as TLR ligands and/or anti CD40/anti-4-1 BB antibodies in a slow release vehicle such as mineral oil (e.g. Montanide ISA 51) or PLGA. Alternatively, the peptides of the invention may be delivered by intradermally, e.g. by injection, with or without immune stimulants (adjuvants). Preferably for intradermal delivery the peptides of the invention are administered in a composition consisting of the peptides and one or more immunologically inert pharmaceutically acceptable carriers, e.g. buffered aqueous solutions at physiological ionic strength and/or osmolarity (such as e.g. PBS).

Intradermal Administration

In a preferred embodiment, a peptide or a composition comprising a peptide or a medicament used in the invention all as defined herein are formulated to be suitable for intradermal administration or application. Intradermal is known to the skilled person. In the context of the invention, intradermal is synonymous with intracutaneous and is distinct from subcutaneous. A most superficial application of a substance is epicutaenous (on the skin), then would come an intradermal application (in or into the skin), then a subcutaneous application (in the tissues just under the skin), then an intramuscular application (into the body of the muscle). An intradermal application is usually given by injection. An intradermal injection of a substance is usually done to test a possible reaction, allergy and/or cellular immunity to it. A subcutaneous application is usually also given by injection: a needle is injected in the tissues under the skin.

In another further preferred embodiment, the medicament used in the invention does not comprise any adjuvant such as Montanide ISA-51, it means the formulation of the medicament is more simple: an oil-water based emulsion is preferably not present in the medicament used. Accordingly, the medicament used in the invention does not comprise an adjuvant such as Montanide ISA-51 and/or does not comprise an oil-in-water based emulsion. Therefore, in a preferred embodiment, the medicament used in the invention is a buffered aqueous solutions at physiological ionic strength and/or osmolarity, such as e.g. PBS (Phosphate Buffer Saline) comprising or consisting of one or more peptide as defined earlier herein. The skilled person knows how to prepare such a solution.

The medicament as used in the invention has another advantage, which is that by intradermally administering low amounts of a peptide as earlier herein defined, an immunogenic effect may still be achieved. The amount of each peptide used is preferably ranged between 1 and 1000 µg, more preferably between 5 and 500 µg, even more preferably between 10 and 100 µg.

In another preferred embodiment, the medicament comprises a peptide as earlier defined herein and at least one adjuvant, said adjuvant being not formulated in an oil-in water based emulsion and/or not being of an oil-in-water emulsion type as earlier defined herein. This type of medicament may be administered as a single administration. Alternatively, the administration of a peptide as earlier herein defined and/or an adjuvant may be repeated if needed and/or distinct peptides and/or distinct adjuvants may be sequentially administered. It is further encompassed by the present invention that a peptide of the invention is administered intradermally whereas an adjuvant as defined herein is sequentially administered. The adjuvant may be intradermally administered. However any other way of administration may be used for the adjuvant.

The intradermal administration of a peptide is very attractive since the injection of the vaccine is realized at or as close by as possible to the site of the disease resulting in the local activation of the disease draining lymph node, resulting in a stronger local activation of the immune system. In particular for VIN, VAIN, AIN, PIN, Penile cancer, Vulva cancer, Anal cancer, Head and Neck cancers.

In a preferred embodiment, the intradermal administration is carried out directly at the site of the lesion or disease. At the site of the lesion is herein understood to be within less than 5, 2, 1, 0.5, 0.2 or 0.1 cm from the site of the lesion.

Upon intradermally administering a medicament as defined herein, not only Th2 but also Th1 responses are triggered. This is surprising since it was already found that cutaneous antigen priming via gene gun lead to a selective Th2 immune response (Alvarez D. et al, 2005 Furthermore, the immune response observed is not only restricted to the skin as could be expected based on (Alvarez D. et al, 2005).

We demonstrate that specific T cells secreting IFNγ circulate through the secondary lymph system as they are detected in the post challenged peripheral blood.

Another crucial advantage of the medicament of the invention is that relatively low amounts of peptides may be used, in one single shot, in a simple formulation and without any adjuvant known to give undesired side-effects as Montanide ISA-51. Without wishing to be bound by any theory, we believe the HPV intradermal peptide(s) used in the invention specifically and directly targets the epidermal Langerhans cells (LC) present in the epithelium. Langerhans cells are a specific subtype of DC which exhibit outstanding capacity to initiate primary immune responses (Romani N. et al 1992). These LC may be seen as natural adjuvants recruited by the medicament used in the invention.

In another preferred embodiment, the invention relates to the use of a peptide derived from HPV-E2, -E6 and/or -E7 protein for the manufacture of a medicament for the treatment or prevention of an HPV related disease, wherein the medicament is for intradermal administration as earlier defined and wherein in addition a peptide derived from HPV-E2, -E6 and/or -E7 protein is further used for the manufacture of a medicament for the treatment or prevention of an HPV related disease, wherein the medicament is for subcutaneous administration.

The medicament for intradermal administration has already been defined herein. The peptide used for subcutaneous administration is the same as the one used for intradermal administration and has already been defined herein. The skilled person knows how to formulate a medicament suited for subcutaneous administration. Preferably, the medicament suited for subcutaneous administration comprises a peptide as already herein defined in combination with an adjuvant. Preferred adjuvants have already been mentioned herein. Other preferred adjuvants are of the type of an oil-in water emulsions such as incomplete Freund's adjuvant or IFA, Montanide ISA-51 or Montanide ISA 720 (Seppic France). In a further preferred embodiment, the medicament suited for subcutaneous administration comprises one or more peptides, an adjuvant both as earlier defined herein and an inert pharmaceutically acceptable carrier and/or excipients all as earlier defined herein. Formulation of medicaments, and the use of pharmaceutically acceptable excipients are known and customary in the art and for instance described in Remington; The Science and Practice of Pharmacy, $21^{nd}$ Edition 2005, University of Sciences in Philadelphia. The second medicament used in the invention is formulated to be suitable for subcutaenous administration.

In this preferred embodiment, the medicament suited for intradermal administration may be simultaneously administered with the medicament suited for subcutaneous administration. Alternatively, both medicament may be sequentially intradermally and subsequently subcutaneously administered or vice versa (first subcutaneous administration followed by intradermal administration). In this preferred embodiment as in earlier preferred embodiment dedicated to the intradermal administration, the intradermal and/or subcutaneous administration of a peptide as earlier herein defined and/or of an adjuvant may be repeated if needed and/or of distinct peptides and/or of distinct adjuvants may be sequentially intradermally and/or subcutaneously administered. It is further encompassed by the present invention that a peptide of the invention is administered intradermally and/or subcutaneously whereas an adjuvant as defined herein is sequentially administered. The adjuvant may be intradermally and/or subcutaneously administered. However any other way of administration may be used for the adjuvant.

We expect the combination of an intradermal and a subcutaneous administration of a medicament according to the invention is advantageous. DC in the epidermis are clearly different from DC in the dermis and in the subcutis. The intracutaneous (intradermal) immunization will cause antigen processing and activation of epidermal DC (Langerin-positive langerhans cells) that through their dendritic network are in close contact with the keratinocytes. This will also optimally activate inflammatory pathways in the interactions between Langerhans cell and keratinocytes, followed by trafficking of antigen loaded and activated Langerhans cell to the skin-draining lymph nodes.

The subcutaneous administration will activate other DC subsets, that will also become loaded with antigen and travel independently to the skin-draining lymph nodes. Conceivably, the use of a medicament which may be administered both intradermally and subcutaneously may lead to a synergistic stimulation of T-cells in these draining nodes by the different DC subsets.

In another aspect, the invention relates to nucleic acids encoding the peptides and/or epitopes as defined herein above. Preferably the nucleic acids do not encode the wild type full length HPV E6 or E7 proteins but rather encode the peptides and/or epitopes of the invention as such, or flanked by amino acid sequence that are not contiguous with the wild type HPV E6 or E7 proteins. Such flanking amino acids may be from proteins other than the wild type HPV E6 or E7 proteins and/or they may be from other locations within the wild type HPV E6 or E7 proteins that are not contiguous with the peptide/epitope they flank. In a preferred embodiment the nucleic acids encode two or more peptides and/or epitopes of the invention arranged as beads-on-string, whereby the peptides and/or epitopes of the invention (the beads) are linked directly together and/or are linked through linker sequences that are from proteins other than the wild type HPV E6 or E7 proteins and/or from other locations within the wild type HPV E6 or E7 proteins that are not contiguous with the peptide/epitope they flank. The amino acid sequences flanking or linking the peptides/epitopes may comprise proteolytic cleavage sites. Such nucleic acids may be applied to deliver the peptides/epitopes of the invention in various ways. They may e.g. be used in the production of recombinant protein in a suitable host cell (e.g. *E. coli*) from which the may be purified. Alternatively the nucleic acid may be operably linked to expression regulatory sequences (promoters and the like) and incorporated in expression constructs for human cells. Such (autologous) cells may be transfected or transduced ex vivo to be (re)-administered to a subject in need thereof. Alternatively the expression construct may be incorporated into suitable gene therapy vector. Viral vector (based on a defective virus) are more efficient agents for gene transfer as compared to the non-viral agents. Suitable viral expression constructs include e.g. vectors that are based on adenovirus, adeno-associated virus (AAV), retroviruses or modified vaccinia Ankara (MVA).

In another embodiment, the present invention provides a tool to isolate HPV-specific T cell receptor (TCR) molecules from T cells capable of interacting with an HPV epitope of the invention as herein described. A TCR according to this invention will preferably be capable of interacting with the HPV epitope comprising peptides when they are in the context of and/or displayed by an HLA molecule, preferably on a living cell in vitro or in vivo. T cell receptors and in particular nucleic acids encoding TCR's according to the invention may for instance be applied to transfer such a TCR into T cells from patients, whom are otherwise not capable to raise T cell immunity against an HPV epitopes of the invention as herein described. By this TCR cloning method, T cell clones may be provided that essentially are isogenic with the recipient to be treated with the T cell clones, i.e. the TCR expression T cell clones are autologous to the patient suffering from an HPV associated disease. The method thus provides T cell clones capable of recognizing an HPV epitope according to the invention that may be generated for and can be specifically targeted to tumor and/or HPV-infected cells expressing an HPV epitope in a subject in need thereof. In a preferred embodiment T-cells from the subject are isolated and transduced with the TCR recognizing the HPV epitopes of the invention as herein described. Following selection and expansion, known to the skilled artisan, these autologous T cells that are now expressing a TCR which can recognize HPV-induced tumor cells or HPV infected cells, can be re-infused into the patient where they specifically target to the tumor and HPV infected cells. Hence, the invention provides T lymphocytes encoding and expressing a T cell receptor capable of interacting with an HPV epitope as defined herein, preferably in the context of an HLA molecule. Said T lymphocyte may be a recombinant or a naturally selected T lymphocyte. T lymphocytes of the invention may also be used for or in the methods and pharmaceutical compositions of the invention. This specification thus provides at least two methods for producing a cytotoxic T lymphocyte of the invention, comprising the step of bringing undifferentiated lymphocytes into contact with an HPV epitope of the invention (or a peptide comprising the epitope) under conditions conducive of triggering an immune response, which may be done in vitro or in vivo for instance in a patient receiving a graft, using peptides according to the invention. Alternatively, it may be carried out in vitro by cloning a gene encoding the TCR specific for interacting with an HPV epitope of the invention, which may be obtained from a cell obtained from the previous method or which may be obtained from a subject exhibiting an immune response against the epitope, into a host cell and/or a host lymphocyte, preferably a autologous lymphocyte, and optionally differentiate to cytotoxic T lymphocyte (CTL). Details of the methods in this embodiment are described in e.g. De Witte et al. 2006 and Schumacher et al. 2002.

In a further embodiment the invention pertains to the use of the nucleic acids encoding the peptides and/or epitopes of the invention, T cell receptors recognizing the epitopes of the invention, nucleic acids encoding such T cell receptors, T cell (clones) expressing such nucleic acids as a medicament. Preferably the medicament is used in the treatment and/or prevention of an HPV associated disease. Such a medicament according to the invention may be used to treat patients suffering from or at risk of developing the following, non extensive list of cervical intraepithelial neoplasia of the cervix (CIN), vulva (VIN), vagina (VaIN), anus (AIN), and penis (PIN), as well as cancer of the cervix, vulva, vagina, anus, penis, and head & neck.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a peptide or a composition as defined herein may comprise additional component(s) than the ones specifically identified, said additional component(s) not altering the unique characteristic of the invention. In addition, reference to an element by the indefinite article "a" or "an"

does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety. The following examples are offered for illustrative purposes only, and are not intended to limit the scope of the present invention in any way

DESCRIPTION OF THE FIGURES

FIG. 1A) Proliferation of initial T cell cultures isolated from cervical tissue from 4 different patients. All T cell cultures recognized naturally processed antigen in a 3-day proliferation assay upon stimulation with HPV16 or 18, E6 or E7 peptide pool and recombinant protein. C265 recognized HPV16E6 peptide pool 1-92, C334 HPV16E6 peptide pool 71-158, C284 HPV16E7 peptide pool 1-98 and C228 HPV18E7 peptide pool 1-106. FIG. 1B) Fine mapping of the specificity of bulk cultures using single peptides was measured by proliferation and IFNγ production. C265 responded to stimulation with peptide HPV16E6 37-68, C334 with HPV16E6 peptide 137-158, C284 with HPV16E7 peptide 71-92 and C228 with HPV18E7 peptide 21-42.

Analysis of the type of T cell responding to HPV antigen as measured by intracellular cytokine staining for IFNγ. For positive peptide and protein, the peptide HPV16E6 41-62 and HPV16E6 protein was used for C265, HPV16E6 protein and peptide 137-158 for C334, HPV16E7 protein and peptide 71-92 for C284 and HPV18E7 protein and peptide 21-42 for C228. Peptides and proteins from HPV counterparts were used as negative controls. The TIL culture of C265 displayed a CD4$^+$ and CD8$^+$ T cell response which both responded to the HPV16 E6 41-62 peptide.

FIGS. 3A-3C

Figure 3A:
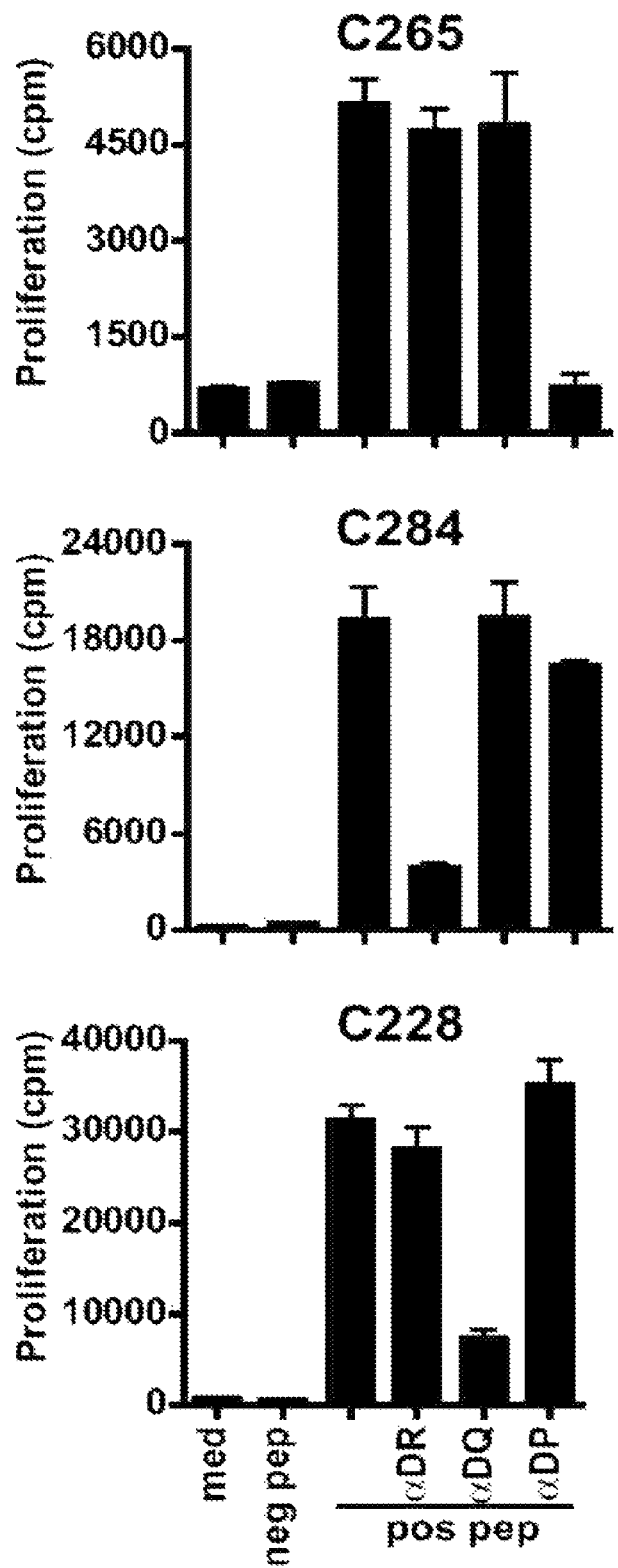
Figure 3B:
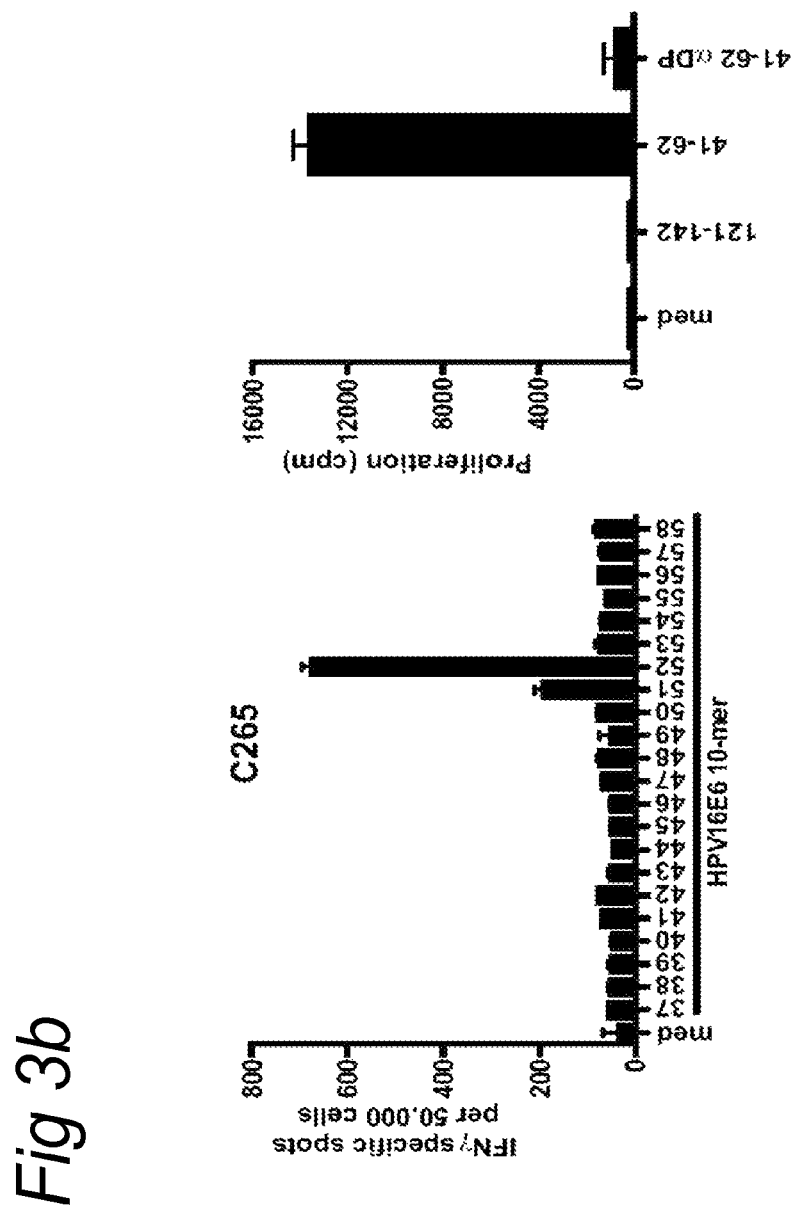
Figure 3C:
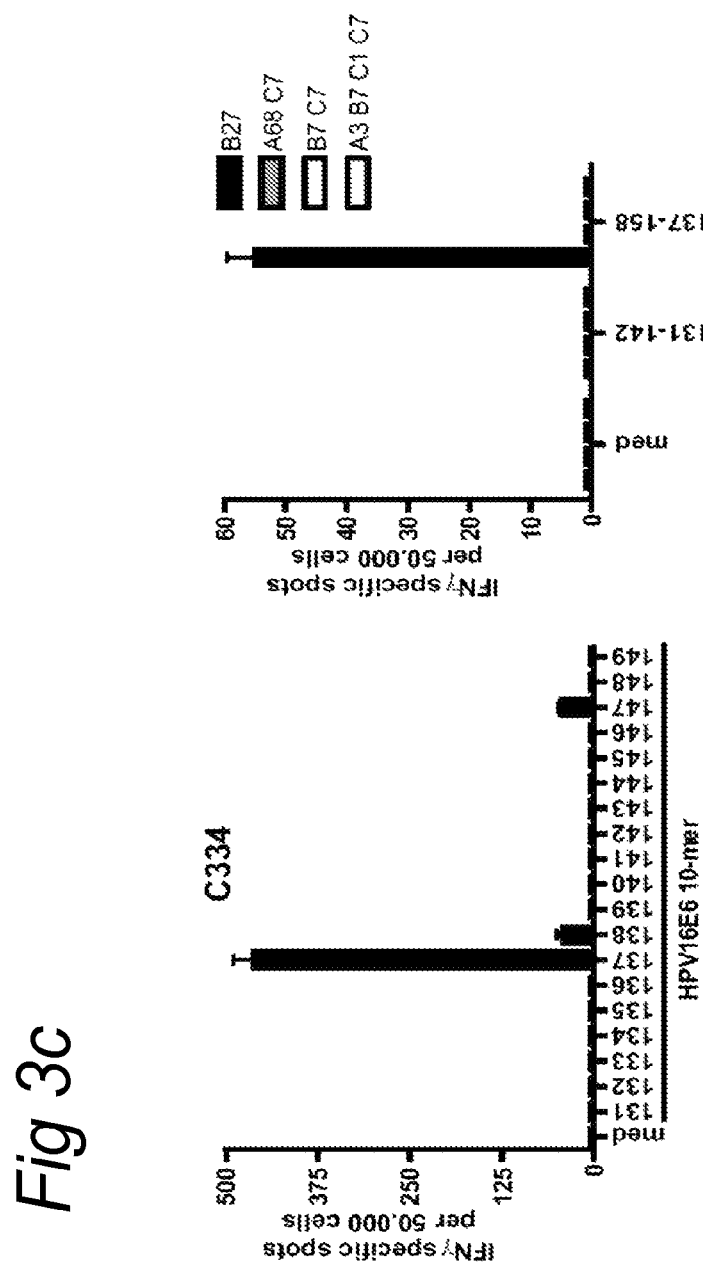

FIG. 3A) Blocking of CD4 restricted responses by HLA class II antibodies in a 3-day proliferation assay. C265 derived T cells were stimulated with peptide loaded autologous B-LCL, C284 derived T cells were stimulated with peptide loaded monocytes that were matched only for HLA-DR12 and C228 derived T cells were stimulated with peptide loaded monocytes, HLA-matched for DQ*0302. FIG. 3B) Fine mapping and HLA restriction of TIL cultures. The CD4$^+$ T cells of patient C265 were stimulated with autologous B-LCL pulsed with 10-mer peptides, covering the amino acid sequence of the recognized longer peptide, was tested in an ELISPOT assay. To determine the restriction of these CD4$^+$ T cells they were stimulated with monocytes matched for HLA-DP2 only. FIG. 3C) Similarly, the minimal peptide-epitope recognized by the CD8 T cells of C334 was determined by incubating these T cells with the indicated 10-mer peptides in an ELISPOT assay. The HLA-restriction of C334 CD8$^+$ T cell response was determined using peptide pulsed PBMC isolated from healthy individuals whom were partially matched with the HLA class I molecules of the patient.

FIGS. 4A-4D

Figure 4A:
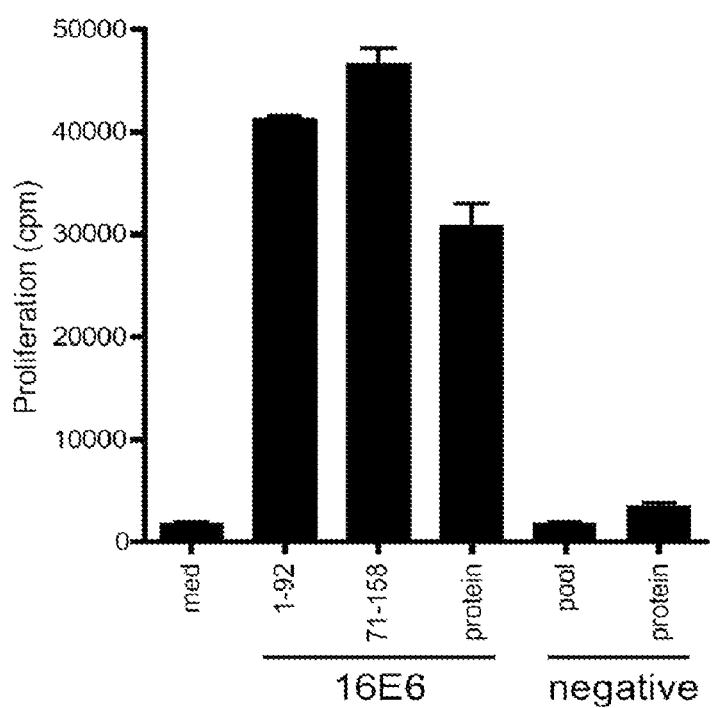
Figure 4B:
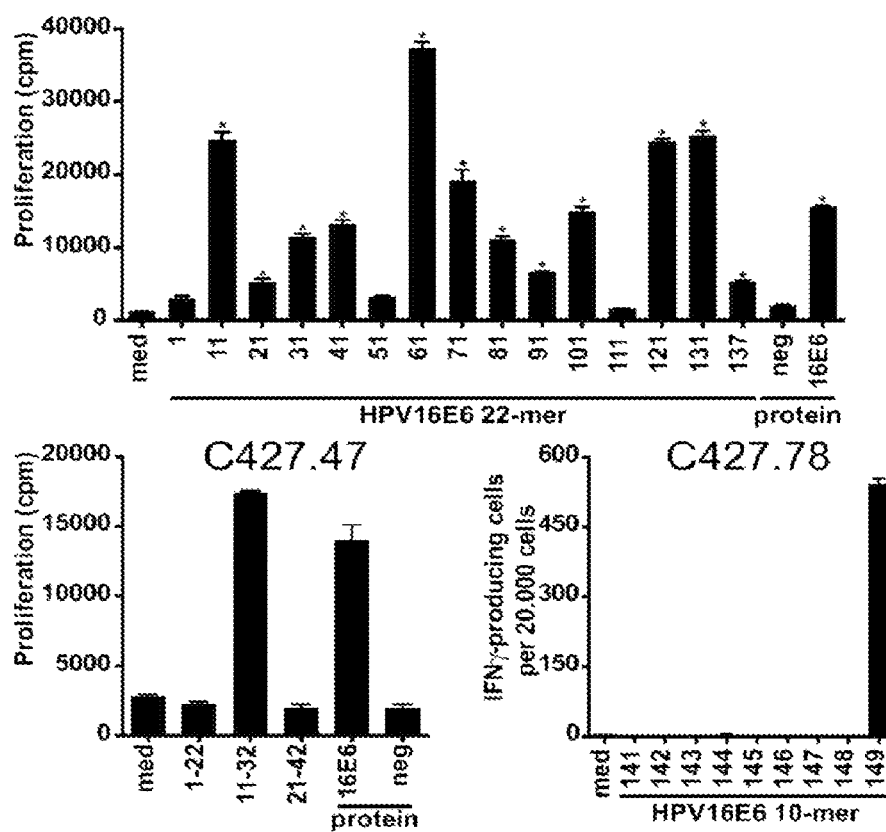
Figure 4D:
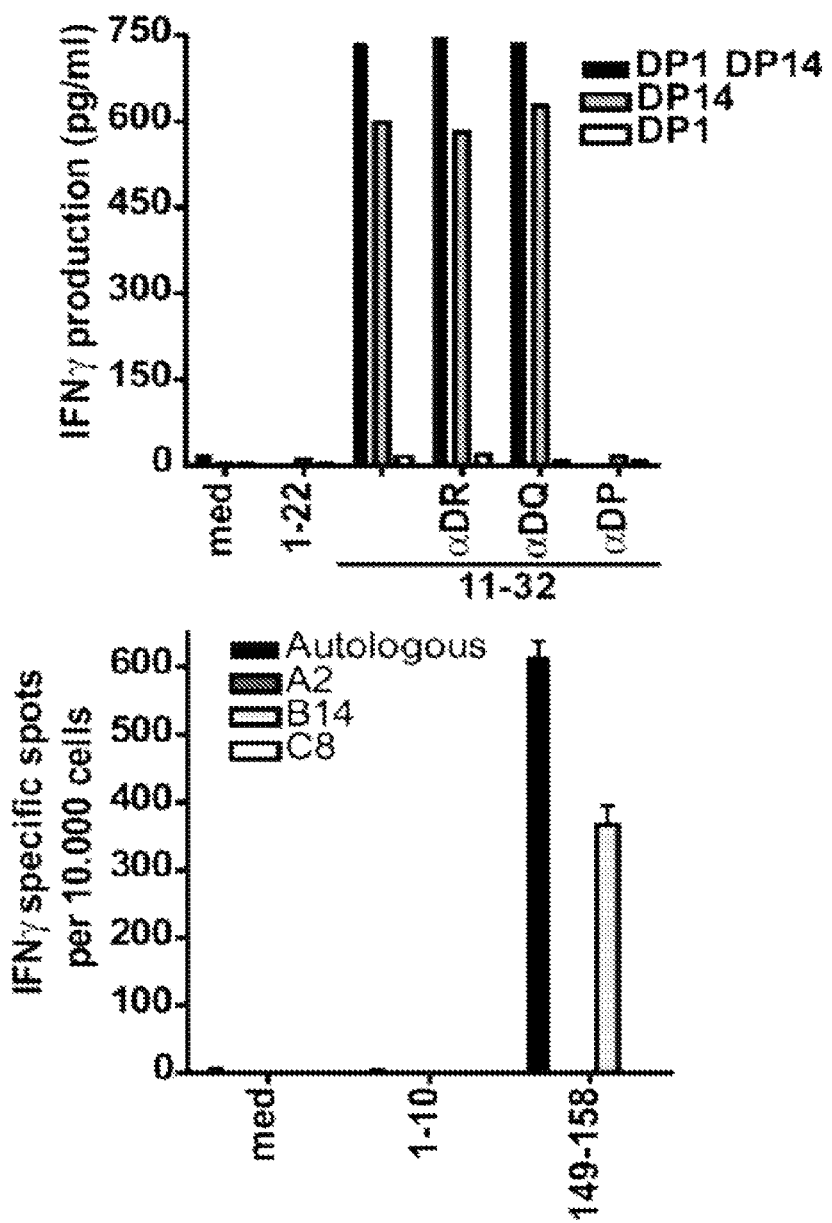

Analysis of T cell reactivity present in tumor draining lymph node of C427. FIG. 4A) Reactivity of T cell cultures after 3 weeks after stimulation with HPV16E6 peptide pulsed autologous B-LCL measured in a 3-day proliferation assay. FIG. 4B) Upper panel: recognition pattern of the T cell culture upon stimulation with autologous B-LCL pulsed with single 22-mer peptides. Lower panels: charting of the minimal epitope recognized by T cell clones that were derived from this initial LNMC culture. CD4 T cell clone C427.47 was stimulated and tested in a 3 day proliferation assay (left panel). The CD8 T cell clone C427.78 was tested in an IFNγ ELISPOT assay (right panel). FIG. 4C) The type of T cell responding was determined by intracellular cytokine staining. HPV16E6 peptide 11-32 (upper panel) and peptide 137-158 (lower panel) were used as positive peptides. HPV18E7 peptide and protein were used as negative controls. FIG. 4D) The restriction element was analyzed using HLA class II blocking antibodies on partially matched B-LCL for class II (C427.47, upper panel) and on partially matched B-LCL for HLA class I (C427.78, lower panel), indicating that the CD4$^+$ T cell response was restricted by HLA-DP14 and the CD8$^+$ T cells by HLA-B14.

FIG. 5

An overview of the number, day of appearance and injected antigen that induced a positive skin reactions in the group of 19 healthy donors (HD). Skin reactions were considered positive when papules greater then 2 mm in diameter arose no less then 2 days after injection. The indicated layout is used for the 8 peptide pools, the first and last amino acid in the protein of the peptide pool used is indicated. The layout printed in bold indicates at least one positive reaction within this timeframe; a filled square represents a new developed, positive skin reaction to the indicated peptide pool.

FIG. 6

Detection of HPV16 specific T cells by IFNγ ELIspot in the pre-challenge blood sample of healthy donors is significantly correlated with the appearance of an early (<13 days) positive skin reaction to the recognized peptide pool (p=0.0003, two tailed Fisher's Extract test). Specific responses were calculated by subtracting the mean number of spots+2×SD of the medium control from the mean number of spots in experimental wells. The number of specific spots per 100.000 PBMC is given. Responses were considered positive if peptide pool specific T cell frequencies were ≥5 in 100.000 PBMCs.

FIG. 7

A. Association between the appearance of a positive skin reaction and the simultaneous detection (IFNγ ELIspot) of circulating HPV16 specific T cells in the post-challenge blood sample of healthy donors (p<0.0001, two tailed Fisher's exact test). From a total of 88 skin tests, 39 were positive. Twenty-five of these 39 reactions were associated with a positive reaction in ELIspot (T cell frequency ≥5 in 100.000 PBMCs). Of the 49 skin test sites that did not show a skin reaction, 10 were associated with a positive ELIspot.

FIG. 8

A. HPV16 specific T cell responses detected by IFNγ ELIspot in the post-challenge blood sample of healthy donors displaying a positive skin reaction. The mean number of spots per 100.000 PBMCs are depicted. Memory response mix (MRM) was used as a positive control. The filled bar indicates the positive skin reaction site of which a punch biopsy was taken and put in to culture.

B. T lymphocytes exfiltrating from punch biopsies were, after a 14- to 28 day period of cytokine driven expansion, tested for their capacity to proliferate upon stimulation with monocytes pulsed with peptides (10 μg/ml)—as injected in the skin test- or with protein (20 μg/ml). Phytohemagglutinine (PHA) served as a positive control. Proliferation was measured by [$^3$H]thymidine incorporation and a proliferative response was defined specific as the stimulation index (SI) ≥3. Healthy donor 17 (HD17) is an example of a positive skin reaction site consisting of non specific T cells.

C. Supernatants of the proliferative responses in B were analysed for the presence of IFNγ, interleukin 4 (IL4), IL5 and tumor necrosis factor α, IL2, IL10 (not shown) by cytometric bead array. Cutoff values were based on the standard curves of the different cytokines (100 pg/ml IFNγ and 20 pg/ml for the remaining cytokines). Antigen-specific cytokine production was defined as a cytokine concentration above cutoff level and >2× the concentration of the medium control. Healthy donor 15 (HD15) displays a high background level of IL5, but is increased >2× after antigen stimulation.

FIG. 9

T cell culture of the skin biopsy of pool 4 ($E6_{41-65}$, $E6_{55-80}$, $E6_{71-95}$) of healthy donor 15 (HD15) consists of both HPV16 specific CD4+ and CD8+ T cells. The specificity of the culture was tested in an intracellular cytokine staining (ICS) against the protein (20 µg/ml) and the peptides (10 µg/ml) corresponding with the injected skin test. Remarkably, in 3 out of 4 biopsies CD8+ HPV16-specific T cells were detected.

EXAMPLES

Example 1: Identification and Characterization of Novel HPV Epitopes

1. Methods
1.1 Subjects

Women presenting with histologically proven cervical neoplasia at the department of Gynaecology of the Leiden University Medical Centre and Leyenburg Hospital the Hague were enrolled in the CIRCLE study, which investigates cellular immunity against HPV16-positive cervical lesions after providing informed consent. The study design was approved by the Medical Ethical Committees of both hospitals. The subjects were tested for HPV status using HPV16 and HPV18 specific primers on DNA isolated from surgical resection specimens (Claas et al. 1989). Peripheral blood mononuclear cells (PBMC) for HLA-restriction analysis were obtained from HLA-typed anonymous healthy blood donors after informed consent.

1.2 Antigens

A set of overlapping peptides spanning both HPV16 and HPV18 E6 and E7 protein were used for T cell stimulation assays. HPV16 and HPV18 E6 and E7 consisted of 22-mers overlapping 12 residues. The peptides were synthesized and dissolved as described earlier (van der Burg et al. 2001, Welters et al. 2006). Recombinant HPV E6 and E7 proteins were produced in recombinant *E. coli* as described earlier (van der Burg et al. 2001). Moreover, a set of overlapping 10-mers (overlapping 9 amino acids) of both HPV16 E6 and E7 was produced to pinpoint the minimal peptide epitope recognized by HPV16-specific T-cells.

1.3 Antigen Presenting Cells

Epstein-Barr virus transformed B cell lines (B-LCL) of the patients were maintained in IMDM containing 10% FCS. Monocytes were generated from peripheral blood lymphocytes as described earlier (de Jong et al. 2002).

1.4 Isolation and Culture of T Cells

Cervical tumor biopsies were obtained after radical hysterectomy, cervical neoplasia tissue was obtained from CIN III patients after biopsy. Fresh cervical tissue was minced in to pieces of approximately 1 mm$^3$ and cultured in IMDM (BioWhittaker, Verviers, Belgium), supplemented with 10% human AB serum (Sigma, St. Louis Mo., USA), 10% T cell growth Factor (TCGF, Zeptometrix, Buffalo N.Y., USA) and 5 ng/ml IL-15 (Peprotech, Rocky Hill N.J., USA). During the first day 5 ng/ml IL-7 (Peprotech) was added to cultures to ensure T cell outgrowth. After 2-3 weeks the specificity of the T cell (TIL, CIL) cultures was tested and positive cultures were expanded using a mix of irradiated autologous B-LCL and 5 µg/ml cognate peptide.

Lymph nodes were derived from the pelvic region and contained tumor cells, indicative of metastatic cancer. The lymph nodes were cut into pieces and incubated for one hour at 37° C. in the presence of collagenase (200 IU/ml, Sigma) and DNAse (50 µg/ml, Sigma), after which the lymph node mononuclear cells were put through a cell strainer (BD, Erebodemgem, Belgium) to obtain a single cell suspension. Separate LMNC cultures were stimulated with HPV16 or 18 E6 or E7 peptide pools and cultured for 2-3 weeks.

T cell clones were isolated using limiting dilution according to a protocol adapted from Evans et al (Evans et al. 2001), replacing IL-2 for 10% TCGF and 5 ng/ml IL-15, and adding 0.5 µg/ml phytohemagglutin (PHA, Murex Diagnostics, Dartford, UK) for T cell receptor triggering. After limiting dilution T cell clones were tested for their specificity and maintained in IMDM containing 10% Fetal Calf Serum (FCS, PAA laboratories, Pasching, Austria), 10% TCGF and 5 ng/ml IL-15. T cell clones were expanded using a mix of culture medium, irradiated PBMC from 3 different donors, B-LCL and 0.5 µg/ml PHA.

1.5 Analysis of T Cell Specificity

T cell cultures (25,000-50,000 cells/well) were tested on pulsed autologous monocytes or irradiated autologous EBVs for the recognition of HPV16 and 18 E6 and E7 peptides (5 µg/ml) and protein (10 µg/ml) in triplicate in a 3 day proliferation assay. After 48 hours supernatant was harvested and stored at −20° C. for cytokine analysis. During the last 16 hours of culture 0.5 µCi/well [$^3$H]thymidine was added to measure proliferation (van der Burg et al. 2001). Antigen specific IFNγ production was measured by ELISA as described earlier (van der Burg et al. 1999).

MHC class II blocking experiments were performed as reported before using murine monoclonal antibodies against HLA-DR (B8.11.2), HLA-DQ (SPV.L3) and HLA-DP (B7/21) (van der Burg et al. 1999). Peptide-pulsed APC were incubated with anti-MHC class II antibodies for 2 hours prior to the addition of T cells.

Enumeration of IFNγ producing T cells as measured by intracellular cytokine staining was performed as described earlier (de Jong et al. 2005). Briefly, APC were loaded with cognate peptide or recombinant protein and incubated with T cell cultures. After 1 hour of incubation 10 µg/ml Brefeldin A (Sigma) was added and incubated overnight. Hereafter the cells were fixed with 4% paraformaldehyde (Sigma) and permeabilized with 0.1% Saponin. The samples were subsequently stained with CD4-APC, CD8-PerCP and IFNγ-PE and analyzed by flow cytometry. The minimal peptide recognized by CD8 T cells was analysed by IFNγ ELISPOT (van der Burg et al. 2001, Welters et al. 2006, de Jong et al. 2002). CD8 T cell lines were seeded in triplicate wells at a density of 2×104 on a Multiscreen 96-well plate (Millipore, Etten-Leur, The Netherlands) coated with an IFNγ catch antibody (Mabtech. Nacha, Sweden). The microcultures were stimulated with 5 µg/ml 10-mer peptides and incubated overnight. Analysis of HLA restriction of CD8 T cells was performed using 5 µg/ml 10-mer peptide pulsed PBMC or B-LCL co-cultured with equal numbers of T cells. IFNγ specific spots were stained according to the instructions of the manufacturer (Mabtech). The number of spots was analysed on a fully automated computer assisted video imaging system (BIOSYS).

2. Results

Figure 1A:
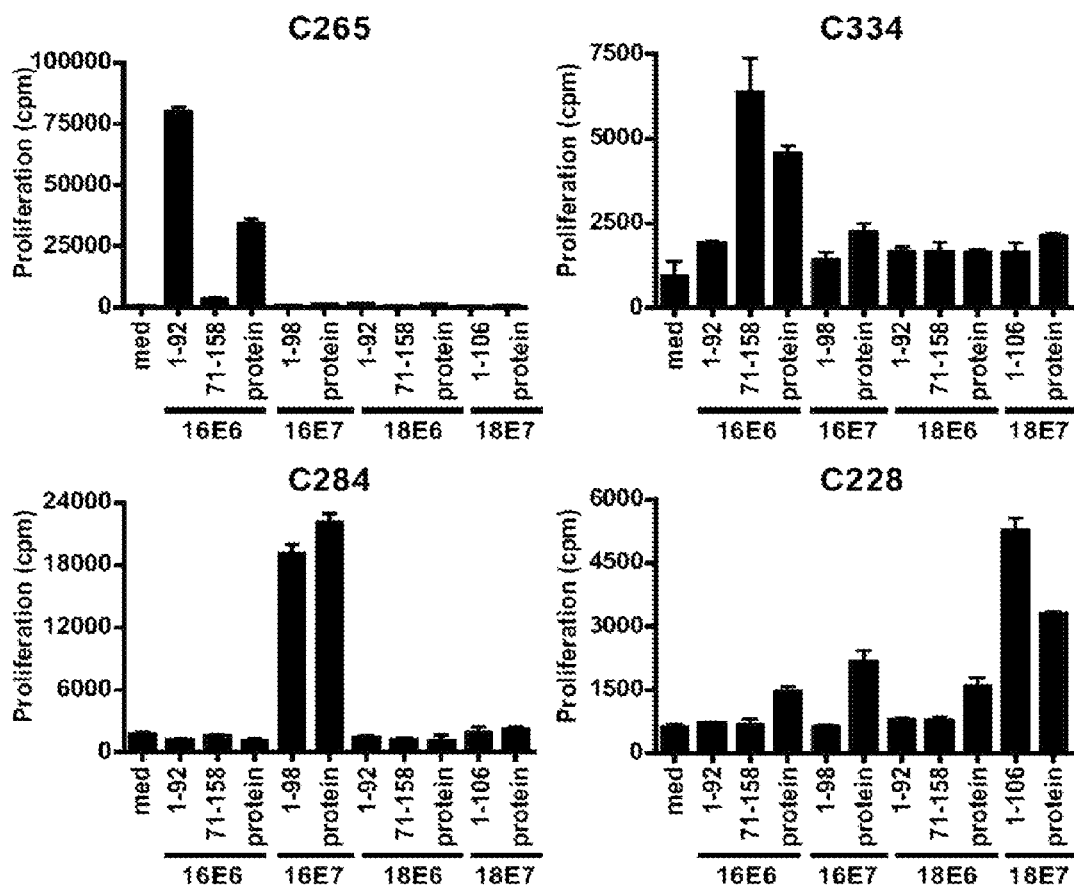
FIGS. 1A and 1B

2.1 HPV-Specific T Cells are Present in Cervical Neoplasia Infiltrating Lymphocytes In the current study we analysed the presence, type and specificity of HPV16 and HPV18-specific T cells in cervical neoplastic lesions, which is the site where HPV-specific T cells encounter their cognate antigen and should exert their effector function. In total 74 patients were analyzed. Cervical tissue was obtained from 61 patients with cervical cancer and from 9 additional patients with CIN III. Minced pieces of tissue were cultured for 2-3 weeks in the presence of a mix of cytokines containing IL-15 and TCGF. To prevent a potential bias in the outgrowth of tumor-specific T cells no exogenous HPV-antigens were provided to these cultures. Within 14-21 days of culture the cytokine expanded T cells were harvested and analysed by FACS. The mean percentage of $CD3^+$ T cells present in these cultures increased from 41% at 2 weeks to 68% at 3 weeks. In general, the culture method did not favour the selective outgrowth of one type of T cell as indicated by the percentage of CD3+CD4+ T cells (34%±22%) and $CD3^+$ $CD8^+$ T cells (52%±22%) at 2 weeks or at 3 weeks (38%±21%; 48%±24%, respectively). Occasionally, an individual culture showed a more pronounced expansion of either $CD4^+$ or $CD8^+$ T cells (not shown). To analyze the presence of HPV-specific T cells, the cultures were stimulated with autologous monocytes pulsed with different pools of overlapping peptides spanning the E6 and E7 proteins of HPV16 and HPV18, as well as with the respective recombinant proteins. In 19 of the 51 HPV16- or HPV18-positive patients we were able to detect HPV-specific T cells by proliferation (Table 1, FIG. 1A). These cultures responded both to peptide and protein loaded monocytes, indicating that the T cells recognized naturally processed antigen. In 8 cultures E6-specific T cells were detected, in 10 cultures the T cells responded to E7 and in one T cell culture a response to both E6 and E7 was detected. Importantly, no HPV16 or 18 specific T cell response was detected in HPV16 and 18 negative cervical tissues (n=19), indicating that the observed HPV16- and 18-specific responses were not induced in vitro (Table 1).

2.2 Both HPV Specific CD4 and CD8 T Cells Infiltrate Tumor Tissue

Figure 1B:
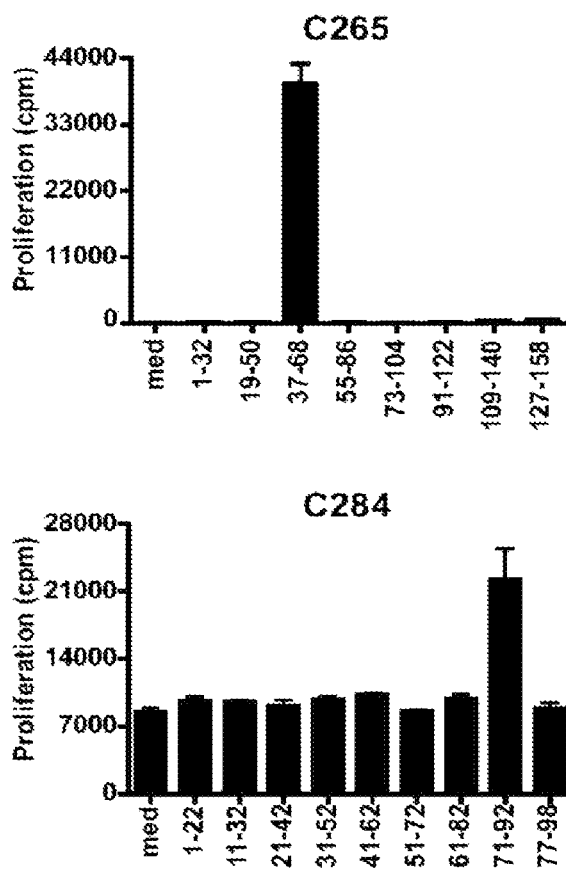
Figure 1B:
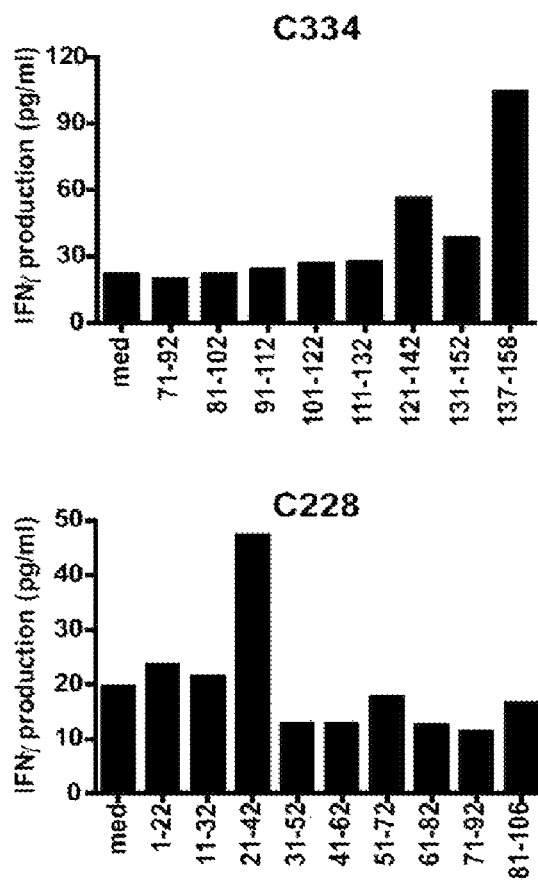
Figure 1B:
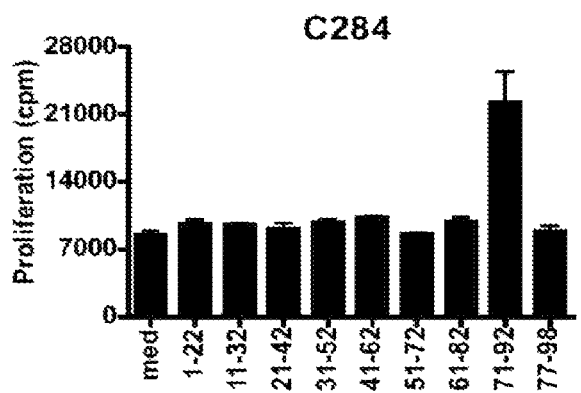
Figure 1B:
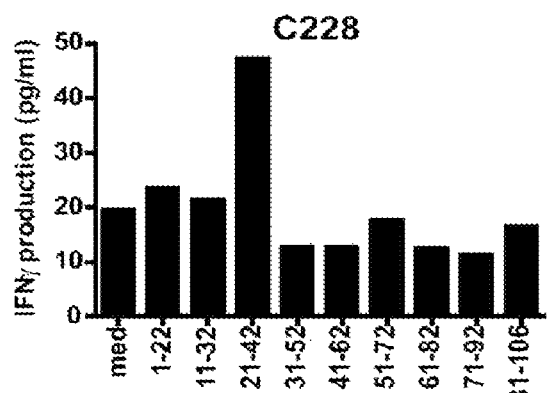
Figure 2:
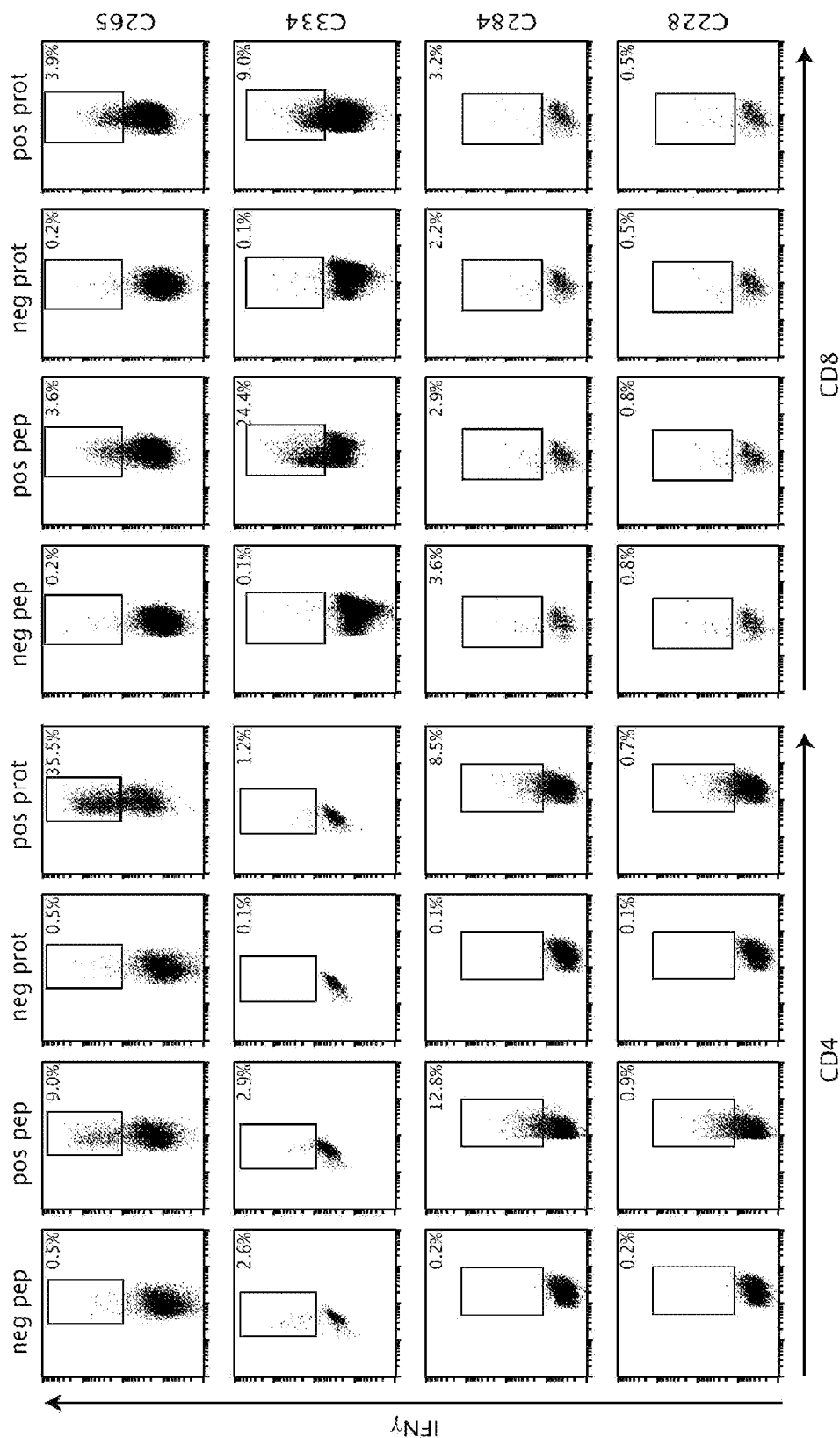
FIG. 2

Following the evaluation of HPV-specific reactivity, the 19 responding T cell lines were expanded by stimulation with cognate peptide, cytokine mix and feeder cells. Fifteen of these HPV-specific cultures could be sufficiently expanded for further analysis. The fine specificity of the HPV-specific T cells was determined in short-term stimulation assays using single peptides. Five cultures recognized 2 or more distinct peptides, whereas the other 10 cultures recognized a single peptide (FIG. 1B, Table 1). To assess the type of T cell that responded to antigenic stimulation, the T cell cultures were stimulated with their cognate peptide and protein antigens and the response was analyzed by intracellular IFNγ staining (FIG. 2). The majority of the TIL cultures contained HPV-specific CD4+ infiltrating T lymphocytes (n=13 patients, 13 different peptides recognized), whereas HPV-specific $CD8^+$ T cells infiltrating lymphocytes were found in 6 cultures. In 9 of the HPV-specific T cell lines only a $CD4^+$ T cell response was detected, in 4 T cell lines both $CD4^+$ T cells and $CD8^+$ T cells reacted and in 2 T cell lines only a CD8 T cells response was detected (Table 1, FIG. 2).

2.3 HLA Restriction of Tumor Infiltrating Lymphocytes

The HLA class I and II loci involved in the presentation of HPV peptides to $CD8^+$ T cells and $CD4^+$ T cells were studied using blocking antibodies and partially HLA matched APC isolated from healthy donors. A wide variety of HLA class II molecules were found to be involved in the presentation of the antigens E6 and E7 of HPV16 and HPV18 (Table 2). The use of blocking antibodies against HLA-DR, HLA-DQ and HLA-DP revealed that 3 of the detected responses were restricted by HLA-DR, 3 by HLA-DQ and 3 by HLA-DP (FIG. 3A, Table 2). To determine the exact HLA restriction element involved in presentation of the HPV antigen, APC from healthy donors that are matched for only one HLA-allele were used (FIGS. 3A-3C). In 6 cases we were not able to exactly determine the restriction element.

In case of patient C265 HPV-specific CD4+ and the CD8+ T cells both responded to the same peptide (FIG. 2). In order to discriminate between these two T cell responses, T cell clones were established through limiting dilution. Unfortunately, only $CD4^+$ T cell clones were obtained and, as such, only the HLA class II-restriction element could be established. Therefore, it was only possible to determine the minimal peptide and restriction in the other 5 different HPV-specific CD8 T cell cultures (Table 2). As an example, FIGS. 3A-3B show the determination of the minimal peptide-epitope and restriction of the CD8 T cell response (FIG. 3C) of the TIL culture obtained from patient C334. This response was restricted by HLA-B27 as this CD8 T cell culture responded only upon stimulation with HLA-B27 matched peptide loaded APC and not with other partially HLA class I matched APC from other donors (FIG. 3C). One patient (C265) displayed a $CD8^+$ T cell response to two different epitopes, and 2 patients (C176 and C334) responded to the same HLA-B27-restricted CTL epitope (Table 2).

2.4 HPV-Specific T Cells in Tumor Draining Lymph Nodes

Tumor draining lymph nodes are the site where HPV-specific T cells are primed and activated and, therefore, the HPV-specific T cell response was also studied in the tumor draining lymph nodes from 6 different cervical cancer patients. Single cell suspensions of lymph node mononuclear cells (LNMC) were isolated from cervical patients displaying metastases in their lymph nodes. We were not able to directly detect HPV specific responses ex vivo in freshly isolated LNMC (data not shown). Therefore, LMNC were first expanded by one round of in vitro stimulation with HPV16 or 18 E6 and E7 peptide pools. In 4 cases the LNMC responded to HPV16 and in 1 patient an HPV18 response was detected by proliferation and IFNγ production (Table 1, FIG. 4A). Similar to the TIL cultures, patients with HPV16-positive tumors reacted only to HPV16 whereas the patient diagnosed with an HPV18-positive cervical cancer reacted only against HPV18. No response to either HPV16 or HPV18 was detected in the LMNC from an HPV16/18-negative patient, despite the fact that the LNMC were stimulated with HPV16 and HPV18 peptides in vitro (Table 1). T cell clones isolated from these LNMC cultures were characterized with respect to their fine specificity and HLA-restriction element. $CD4^+$ T cell reactivities were found to 10 different peptides, 7 of which were not detected in the TIL cultures. Three of these epitopes were restricted by HLA-DQ and the other 4 by HLA-DP. In addition, one HLA-A*0201-restricted and one HLA-B14-restricted CD8+ T cell epitope was identified (Table 2). FIG. 4 shows an example of the analysis of a LNMC culture. After one round of stimulation the LNMC cultures specifically responded to APC loaded with pools of HPV16E6 peptides or recombinant protein (FIG. 4A). Analysis of the reactivity against single peptides showed recognition of a broad repertoire of peptides (FIG. 4B) and the $CD4^+$ and $CD8^+$ T cell clones isolated from this culture recognized their cognate antigen when naturally processed from recombinant protein (FIG. 4C). The restriction was further determined using HLA class II blocking antibodies and APC form partially matched donors (FIG. 4D).

Taken together, the analysis of both TIL and tumor-draining lymph node cells revealed that in 23 of the 54 different HPV16 or HPV18 positive patients a specific T cell response to in total 25 different E6- or E7-derived peptides can be detected. Notably, 13 CD4+ T cell peptide-epitopes were restricted by HLA-DQ or HLA-DP, 3 by HLA-DR and in 6 cases we were not able to distinguish between HLA-DQ/DP and HLA-DR (Table 2). Of the CD8+ T cell responses found, 2 were restricted by HLA-A, 4 by HLA-B and 2 were undetermined (Table 2).

3. Discussion

The HPV16 encoded oncoproteins E6 and E7 can serve as tumor rejection antigens in animal models (Zwaveling et al. 2002, Peng et al. 2005) suggesting that they may also serve as target antigens for tumor-infiltrating lymphocytes in cervical cancer, but this has never been systematically analyzed in a large group of patients. We were able to establish a high number of TIL and CIN-infiltrating lymphocytes (CIL) cultures reactive against HPV16 and HPV18, which are the HPV types most prominently associated with cervical cancer (Bosch et al. 1995, Munoz et al 2003). The cytokine mix used ensured the outgrowth of both CD4 and CD8 T cells without an overt preference for the expansion of either type of T cell. In the course of our study 19 TIL cultures were established from patients diagnosed with a tumor positive for an HPV type other than HPV16 or HPV18. None of these cultures reacted to stimulation with HPV16 or HPV18 E6 and E7 antigens. Notably, TIL and CIL from HPV16-positive patients did not respond to E6 and E7 of HPV18 and vice versa (Table 1). Therefore, the observed HPV-specific T cell responses in the TIL and CIL of HPV16- or HPV18-positive patients are not the result of in vitro induced T cell responses but a reflection of the anti-tumor response in vivo. Recently, we showed that this protocol was also successful in the expansion of TIL cultures from a small cohort of patients with ovarian cancer (Lambeck et al. 2007).

Similar numbers of TIL cultures responded to E6 and E7 (Table 1). Identification of the cognate peptide-epitopes and HLA-restriction elements of the HPV-specific immune responses revealed that HPV-specific immunity was not restricted to a specific immunodominant region but was aimed at all domains of the E6 and E7 oncoproteins (Table 2), suggesting that both HPV E6- and E7-specific T cells will contribute to the anti-tumor response. Strikingly, our analysis revealed that the great majority of the HPV-specific CD4+ T cell responses were restricted by HLA-DQ or DP (13/16) and not by HLA-DR (Table 2). This was unexpected because HLA-DR is the most abundant HLA class II molecule on the cell surface of APC (Schwatz et al. 1988) as well as on cervical cancer cells with de novo HLA class II expression (Hilders et al. 1994). Furthermore, in other tumor antigens most of the CD4+ T cell epitopes identified are presented in the context of HLA-DR (80/93; see database on http://www.cancerimmunity.org). However, in cervical cancer there seems to exist a more prominent role for HLA-DQ and HLA-DP restricted T cells, arguing that strategies, incorporating computer algorithms, to identify functional T cell responses against HPV should not be focused on HLA-DR only (Warrino et al. 2004, Facchinetti al. 2005). In 7 patients a CD8+ T cell response was detected. In addition to the identification of 3 novel HLA-B7, HLA-B14 and HLA-B27 restricted CD8 T cell epitopes, we confirmed the presence of HLA-A*0201-restricted tumor-infiltrating CD8+ T cells recognizing the HPV16 E7.11-20 epitope (Evans et al. 1997, Oerke et al. 2005), albeit that stronger reactivity was observed against the peptide sequence 11-19. In addition, CD8+ T cells reactive to the HLA-B57 restricted epitope HPV16E6.52-61 were detected. Based on the detection of HLA-B57-restricted HPV16E6.52-61-specific CD8+ T cells in the peripheral blood of healthy subjects it has been suggested that this CTL epitope may play an important role in clearing HPV16-infection (Nakagawa et al 2004, Nakagawa et al 2007). However, the detection of CTL responding to this epitope in cancer patients makes this less likely.

Our study shows that in at least 23 of the 54 different HPV16 or HPV18 positive patients, a specific T cell response to E6 and/or E7 can be detected (Table 1). This will facilitate vaccination strategies aiming at the induction of a T cell response to these antigens to reinstate an effective anti-tumor response in those patients with a pre-existing immune response. Importantly, the T cell epitopes recognized by the T cells in this study constitute physiological targets in the immune response to HPV16 and HPV18 positive tumors. As such they will be valuable for the integrated analysis of the magnitude and functionality of HPV-specific T cell subsets at different stages of disease and monitoring immunotherapy. The frequent presence of HPV-specific T cells in cervical cancer patients may also constitute a valuable source of tumor-specific T cells that can be used in adoptive T cell transfer therapies.

Example 2: Intradermal Administration of a Peptide

Materials and Methods

Study Design

A cross-sectional pilot study to analyse HPV16 E2-, E6-, and E7-specific T-cell responses as measured by intradermal injection of pools of clinical grade HPV16 peptides in the upper arm was performed in patients with HPV-related disorders of the cervix and in healthy individuals. Since a delayed type hypersensitivity reaction represents a memory T-cell response, there was no prerequisite for HPV16-positivity at the time of analysis.

Subjects

A group of nineteen healthy individuals (HD) participated in this study after providing informed consent. The group of healthy individuals displayed a median age of 31 years old (range, 20-51 years) and was comprised of 80% women and 20% males. Peripheral blood mononuclear cells (PBMCs) were obtained from all subjects immediately before administration of the skin test. The late appearance of positive skin tests in healthy individuals resulted in the isolation of a second blood sample from 11 of 19 healthy volunteers. The study design was approved by the Medical Ethical Committee of the Leiden University Medical Centre.

DTH Skin Test

Skin tests, based on Delayed Type Hypersensitivity reactions (DTH), can be used as a sensitive and simple method for in vivo measurement of HPV-specific cellular immune responses (Hopfl, 2000; Hopfl, 1991). The skin test preparations consisted of 8 pools of long clinical-grade synthetic peptides spanning the whole HPV 16 E6 and E7 protein and the most immunogenic regions of HPV 16 E2 protein (de Jong, 2004). These clinical grade peptides were produced in the interdivisional GMP-Facility of the LUMC. Each pool of the skin test consisted of 2 or 3 synthetic peptides, indicated by the first and last amino acid of the region in the protein covered by the peptides. Pool 1: $E2_{31-60}$, $E2_{46-75}$, Pool 2: $E2_{301-330}$, $E2_{316-345}$, Pool 3: $E6_{1-31}$, $E6_{19-50}$ (SEQ ID NO:

28), Pool 4: $E6_{41\text{-}65}$ (SEQ ID NO: 29), $E6_{55\text{-}80}$ (SEQ ID NO: 30), $E6_{71\text{-}95}$ (SEQ ID NO: 31), Pool 5: $E6_{85\text{-}109}$ (SEQ ID NO: 32), $E6_{91\text{-}122}$ (SEQ ID NO: 33), Pool 6: $E6_{109\text{-}140}$ (SEQ ID NO: 34), $E6_{127\text{-}158}$ (SEQ ID NO: 35), Pool 7: $E7_{1\text{-}35}$ (SEQ ID NO: 36), $E7_{22\text{-}56}$ (SEQ ID NO: 37), Pool 8: $E7_{43\text{-}77}$ (SEQ ID NO: 38), $E7_{64\text{-}98}$ (SEQ ID NO: 39). Pool 3 comprises Seq ID 5, 22 and 23. Pool 4 comprises Seq IDs 7-9. Pool 5 comprises Seq IDs 11 and 12. Pool 6 comprises Seq IDs 13, 14, 24 and 25. Pool 7 comprises Seq ID 15 and 26. Pool 8 comprises Seq IDs 16 and 17. Per peptide pool 0.05 ml of 0.2 mg/ml peptides in 16% DMSO in 20 mM isotonic phosphate buffer (10 µg/peptide) was injected intracutaneously. The pools of peptides and a negative control (dissolvent only) were injected separately at individual skin test sites of the upper arm. Skin test sites were inspected at least three times, at 72 hours and 7 days after injection (Hopfl) of the peptides and at 3 weeks following the first report of a very late skin reaction in one of the first healthy subjects. Reactions were considered positive when papules greater than 2 mm in diameter arose no less than 2 days after injection. From positive skin reaction sites punch biopsies (4 mm) were obtained, cut in small pieces and cultured in IMDM containing 10% human AB serum, 10% TCGF and 5 ng/ml IL7 and IL15 to allow the emigration of lymphocytes out of the skin tissue. After 2 to 4 weeks of culture the expanded T cells were harvested and tested for their HPV-specific reactivity.

Antigen for In Vitro Immune Assays

A set of peptides, similar to the peptides used in the skin test, were used for T—cell stimulation assays and IFNγ-ELISPOT assays. The four HPV 16 E2 peptides consisted of 30-mer peptides overlapping 15 residues, HPV 16 E6 consisted of 32-mers and HPV 16 E7 of 35-mers, both overlapping 14 residues. The peptides were synthesized and dissolved as previously described (van der Burg, 1999). Notably, in the IFNγ ELISPOT assays peptide pool 4 and 5 slightly differed from the peptide pools used in the skin test, pool 4 contained peptides $E6_{37\text{-}68}$, $E6_{55\text{-}86}$, $E6_{73\text{-}104}$ and pool 5 comprised peptides $E6_{73\text{-}104}$, $E6_{91\text{-}122}$.

Memory response mix (MRM 50×), consisting of a mixture of tetanus toxoid (0.75 *Limus flocculentius*/ml; National Institute of Public Health and Environment, Bilthoven, The Netherlands), *Mycobacterium tuberculosis* sonicate (5 µg/ml; generously donated by Dr. P. Klatser, Royal Tropical Institute, Amsterdam, The Netherlands), and *Candida albicans* (0.15 mg/ml, HAL Allergenen Lab., Haarlem, The Netherlands) was used as a positive control. Recombinant HPV 16 E2, E6 and E7 proteins were produced in recombinant *Escherichia coli* as described previously (van der Burg, 2001).

Analysis of Antigen-Specific Th Cells by IFNγ ELISPOT

The presence of HPV 16-specific Th Cells was analyzed by ELISPOT as described previously (van der Burg, 2001) Briefly, fresh PBMCs were seeded at a density of $2 \times 10^6$ cells/well of a 24-well plate (Costar, Cambridge, Mass.) in 1 ml of IMDM (Bio Whittaker, Verviers, Belgium) enriched with 10% human AB serum, in the presence or absence of the indicated HPV 16 E2, E6 and E7 peptide pools. Peptides were used at a concentration of 5 µg/ml/peptide. After 4 days of incubation at 37° C., PBMCs were harvested, washed, and seeded in four replicate wells at a density of $10^5$ cells per well in 100 µl IMDM enriched with 10% FCS in a Multiscreen 96-well plate (Millipore, Etten-Leur, The Netherlands) coated with an IFNγ catching antibody (Mabtech AB, Nacha, Sweden). Further antibody incubations and development of the ELISPOT was performed according to the manufacturer's instructions (Mabtech). Spots were counted with a fully automated computer-assisted-video-imaging analysis system (Bio Sys). Specific spots were calculated by subtracting the mean number of spots+2×SD of the medium control from the mean number of spots in experimental wells (van der Burg, 2001).

T Cell Proliferation Assay

T-cell cultures of the skin biopsies were tested for recognition of the specific peptides and protein in a 3-day proliferation assay (van der Burg, 2001). Briefly, autologous monocytes were isolated from PBMCs by adherence to a flat-bottom 96-well plate during 2 h in X-vivo 15 medium (Cambrex) at 37° C. The monocytes were used as APCs, loaded overnight with 10 µg/ml peptide and 20 µg/ml protein. Skin test-infiltrating-lymfocytes were seeded at a density of $2\text{-}5 \times 10^4$ cells/well in IMDM supplemented with 10% AB serum. Medium alone was taken along as a negative control, phytohemagglutinine (0.5 µg/ml) served as a positive control. Proliferation was measured by $[^3H]$ thymidine (5 µCi/mmol) incorporation. A proliferative response was defined specific as the stimulation index (SI) ≥3. Supernatants of the proliferation assays were harvested 48 hours after incubation for the analysis of antigen-specific cytokine production.

Analysis of Cytokines Associated with HPV16-Specific Proliferative Responses

The simultaneous detection of six different Th1 and Th2 cytokines: IFNγ, tumor necrosis factor α, interleukin 2 (IL2), IL4, IL5 and IL10 was performed using the cytometric bead array (Becton Dickinson) according to the manufacturer's instructions. Cut-off values were based on the standard curves of the different cytokines (100 pg/ml IFNγ and 20 pg/ml for the remaining cytokines). Antigen-specific cytokine production was defined as a cytokine concentration above cutoff level and >2× the concentration of the medium control (de Jong, 2004).

Intracellular Cytokine Staining (ICS)

The specificity and character of the T cell cultures derived from positive skin reaction sites was tested by ICS as reported previously (de Jong, 2005). Briefly, skin test infiltrating lymphocytes were harvested, washed and suspended in IMDM+10% AB serum and $2\text{-}5 \times 10^4$ cells were added to autologous monocytes that were pulsed overnight with 50 µl peptide (10 µg/ml) or protein (20 µg/ml) in X vivo medium. Medium alone was taken along as a negative control, phytohemagglutinine (0.5 µg/ml) served as a positive control. Samples were simultaneously stained with FITC-labelled mouse-antihuman IFNγ (0.5 g/ml, BD PharMingen), PE-labelled mouse-antihuman IL5 (0.2 mg/ml, BD PharMingen), APC-labelled anti-CD4 (BD Bioscience) and PerCP-labelled anti-CD8 (BD Bioscience). After incubation at 4° C., the cells were washed, fixed with 1% paraformaldehyde and analyzed by flow cytrometry (FACSscan, BD Biosciences)

Statistical Analysis

Fisher's Exact test (2-tailed) was used to analyze the relationship between the detection of IFNγ-producing HPV-specific T-cells in PBMC, the presence of a skin test reaction or the presence of HPV-specific T-cells in skin biopsies, as well as differences between patients and healthy controls with respect to the size or the number of the skin reactions within these groups. Statistical analyzes were performed using Graphpad Instat Software (version 3.0) and Graphpad Prism 4.

Results

Skin Reactions to Intracutaneous Injection with HPV 16 E2, E6- and E7 Peptides

Figure 5:
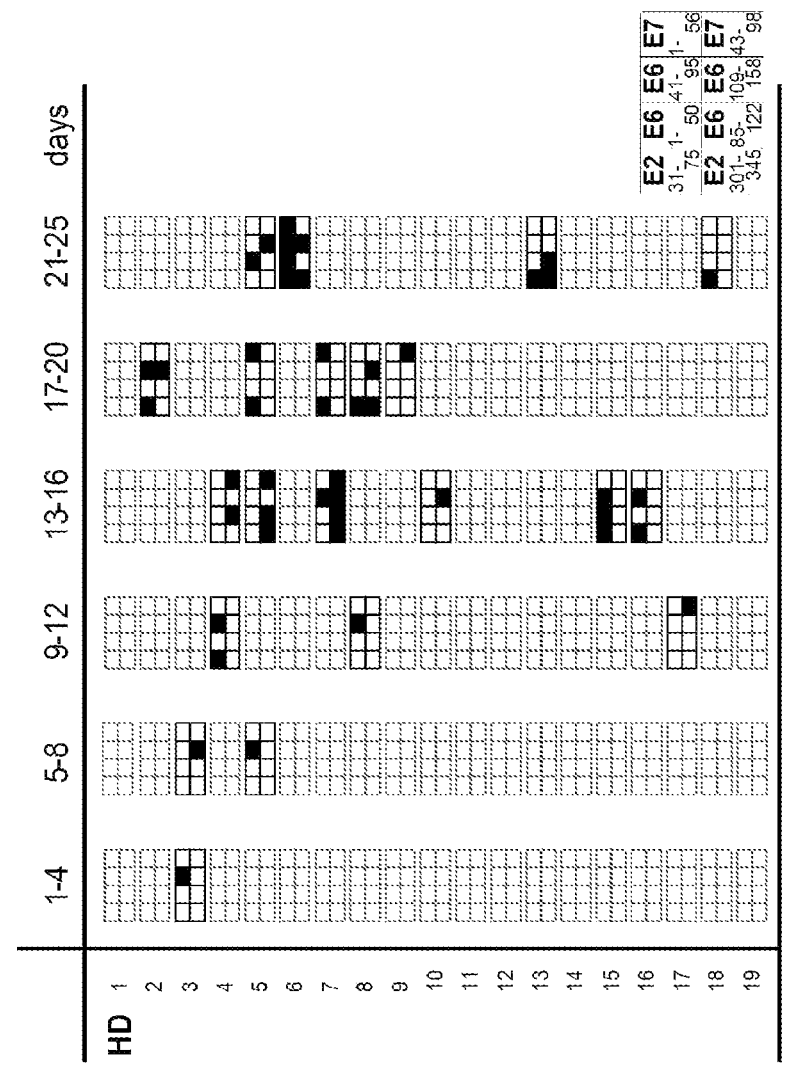

We studied skin reactions in healthy subjects after intracutaneous injection with HPV16 E2, -E6 and -E7 peptides. Positive skin reactions appeared as flat reddish papules of 2 to 20 mm of diameter, arising within 2 to 25 days after injection. A positive skin reaction was detected in 46 of the 152 skin tests in the healthy volunteers. Over all, each peptide-pool in the skin test could give rise to a positive skin reaction. Most frequently reactions against $E2_{31-75}$ (10 out of 19 subjects), $E6_{37-104}$ (9/16) and $E7_{43-98}$ (7/19) were observed in the control group. This reaction pattern resembles that of what we previously observed in PBMC (de Jong, 2002; Welters, 2003) (FIG. 5). These skin reactions corresponded with the presence of a peptide specific T cell response as detected in the PBMC of these individuals (data not shown).

Skin Reactions in Healthy Donors are Associated with Higher Frequencies of HPV 16-Specific T-Cells in the Peripheral Blood.

Figure 6:
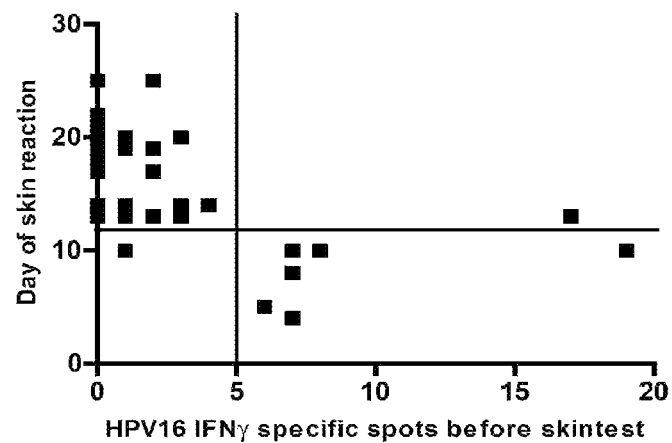

In order to compare the results of the skin test with the presence of circulating HPV16-specific type 1 T cells, an IFNγ ELIspot assay was performed with PBMC's collected before the intradermal peptide-challenge was given. In 5 out of 19 healthy volunteers we were able to detect a HPV16-specific immune response by IFNγ-ELIspot. The detection of ≥5 circulating HPV16-specific T-cells per 100.000 PBMC in the pre-challenge blood sample of healthy individuals was associated with an early (≤13 days) positive skin reaction to the same peptide sequence (p=0.0003, two tailed Fisher's exact test; FIG. 6). No HPV16-specific circulating T-cells were detected in the pre-challenge blood sample healthy donors to peptides that induced a late positive skin reaction (14 to 25 days). This suggests that the frequency of circulating antigen-specific cells determine the delay time for skin reactions to appear.

Figure 7:
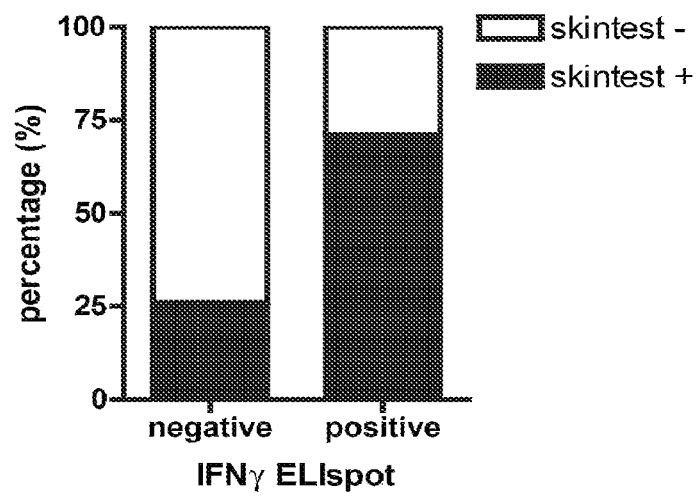

In order to assess the frequency of HPV-specific T-cells at the time that a late skin reaction appeared additional blood samples from 11 healthy volunteers were collected. In these individuals 39 out of 88 skin tests were positive. In 25 of the 39 positive skin reactions and in 10 of 49 negative skin reactions ≥5 HPV16-specific T-cells were detected per 100.000 PBMC. At this point a significant correlation was found between the detection of circulating HPV-specific IFNγ-producing T-cells in the post-challenged blood sample and the presence of a skin reaction (p<0.0001, Fisher's exact test; FIG. 7). This shows that the frequency of HPV16-specific T cells in the blood of healthy volunteers is significantly higher following an intradermal challenge with HPV16 peptide and indicates that intracutaneous injection of peptide antigens enhances the number of HPV16-specific T cells in the blood of healthy volunteers.

Biopsies of Positive Skin Reaction Sites Consist of Both Th1/Th2– CD4+ and CD8+ HPV16-Specific T Cells.

Approximately 25% of the positive skin reactions of healthy volunteers were not associated with the detection of HPV16-specific IFNγ-producing T-cells in the blood, suggesting that other, non IFNγ-producing types of T-cells may infiltrate the skin after intradermal injection of HPV16 peptides.

Figure 8:
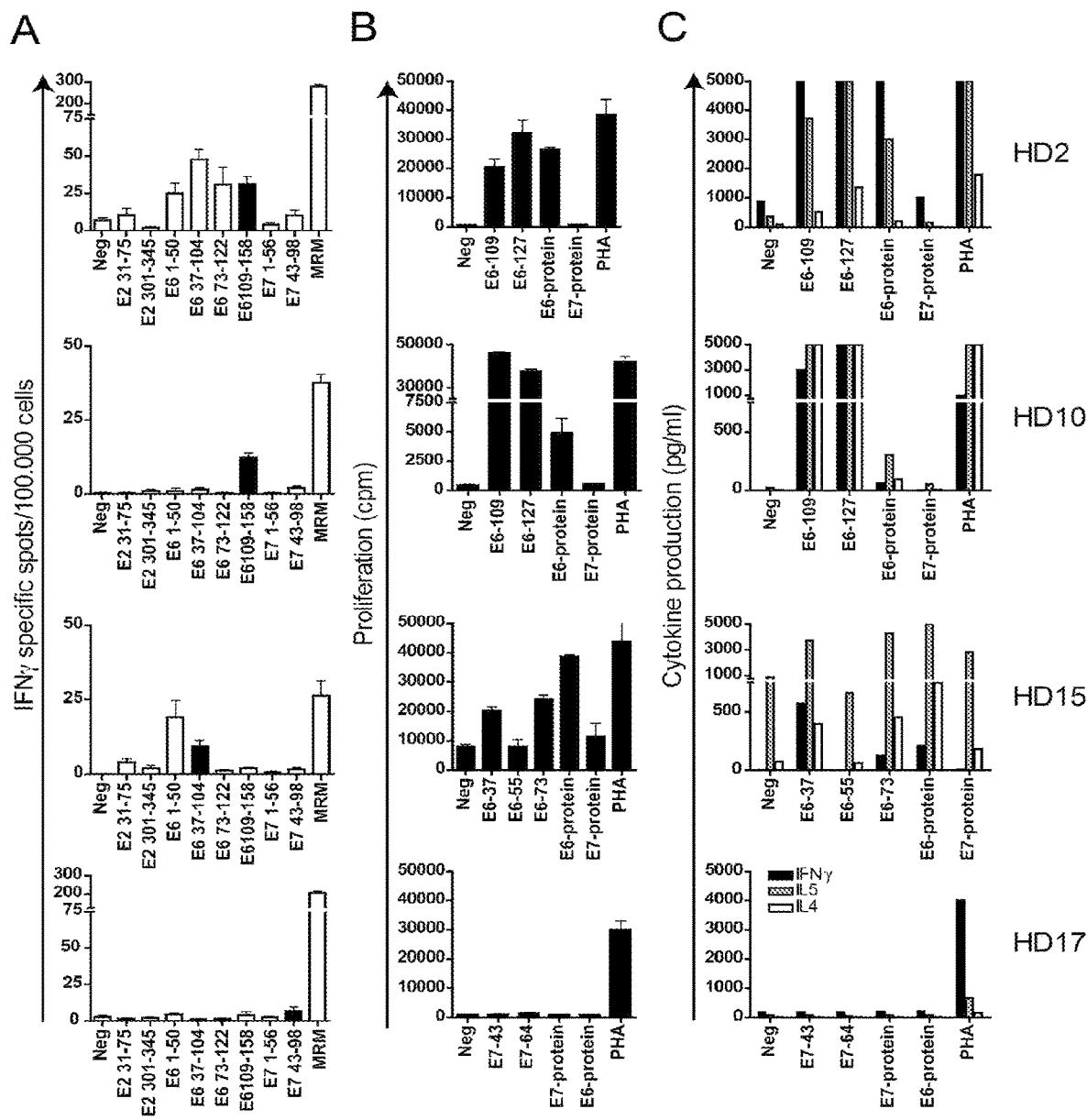

In order to characterize the cells in a positive skin reaction site punch biopsies were taken. In total, 8 biopsies were taken from different positive skin reaction sites of 7 healthy controls and cultured with a cocktail of cytokines that allowed the outgrowth of T-cells in vitro without antigenic stimulans. In 7 of 8 cases, T-cells ex-filtrated the tissue and expanded within 3-4 weeks. The expanded T-cells were tested for their specificity in a short term proliferation assay. FIG. 8 shows examples of T-cell cultures that specifically proliferated upon stimulation with autologous monocytes pulsed with the pool of peptides, also injected in this site during the skin test (HD2, HD10, HD15) as well as to monocytes pulsed with HPV16 E6 protein (FIG. 8). This indicates that these T-cells were capable of recognizing their cognate HLA-peptide complexes after the antigen was naturally processed and presented. Analysis of the supernatants of these proliferative T-cell cultures revealed a mixed Th1/Th2 cytokine profile in that the HPV16-specific T-cells produced IFNγ, IL-4 and IL-5 (FIG. 8).

In each case that HPV-specific T-cells were detected in the biopsy culture (4 out of 8) this coincided with the detection of circulating HPV16-specific IFNγ-producing T-cells in the post-challenge blood sample by ELIspot (compare FIGS. 8, A and B). In 3 of the other 4 positive skin reaction biopsies (HD2, HD17, HD18) the T-cells did not respond to HPV16 peptides (FIG. 8; HD17) and in one case no T-cells ex-filtrated the tissue at all (HD13). In these 4 cases we were not able to detect circulating HPV16-specific IFNγ-producing T-cells in the post-challenge blood sample.

Figure 9:
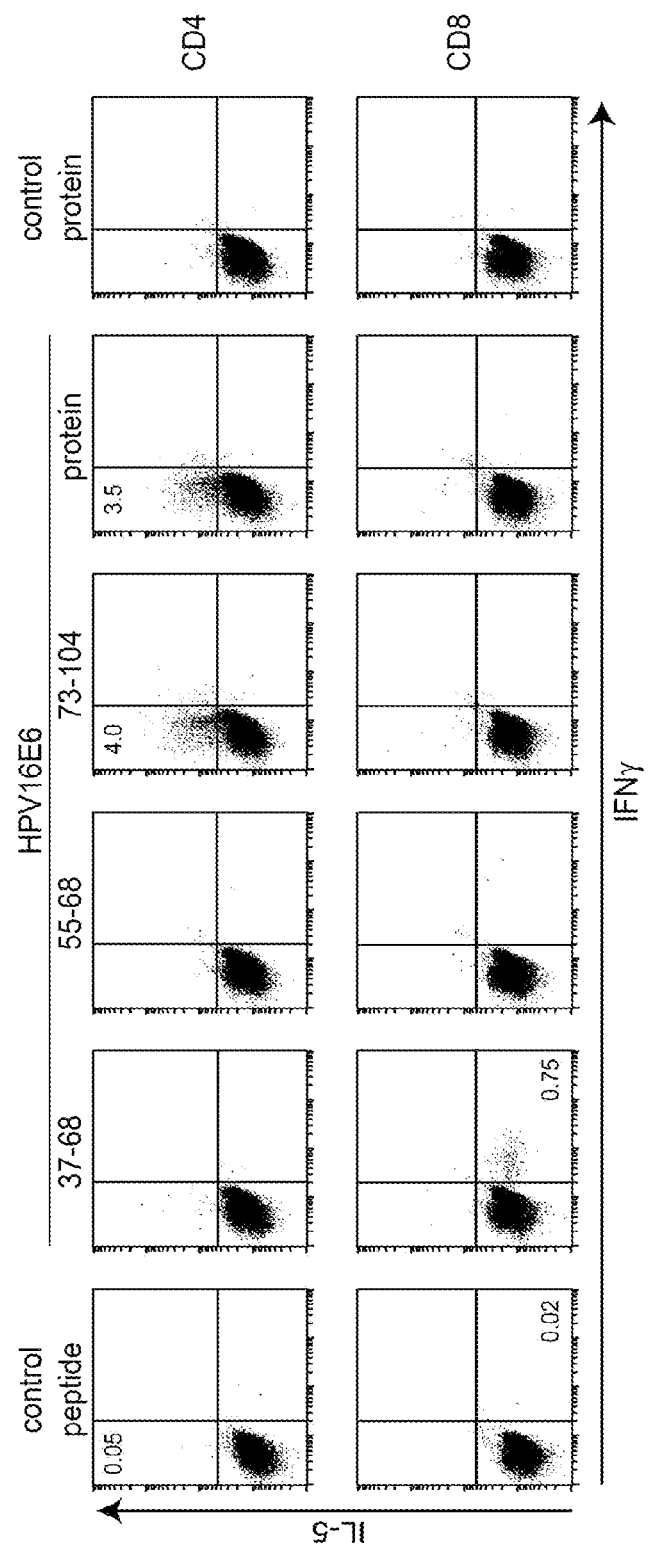

Co-staining of the biopsy-T cells by CD4 and CD8 cell surface markers showed that not only HPV16-specific CD4+ but also HPV16-specific CD8+ T cells infiltrated the skin site upon intradermal challenge with HPV16 peptide (FIG. 9). Overall, in 3 out of 4 biopsies infiltrated by HPV16-specific T-cells, we were able to detect HPV16-specific CD8+ T cells. The CD8+ T cells isolated from the biopsy (pool 6) of HD2 responded to both overlapping peptides of the injected skin test: HPV16 $E6_{109-140}$ and $E6_{127-158}$ (data not shown), while the CD8+ T cells of both subjects HD15 and HD16 responded to HPV16 $E6_{37-68}$ (see example for HD15, FIG. 5).

Taken together, the population of immune cells migrating into the skin upon an intradermal challenge with HPV16 peptides comprises HPV16-specific CD4+ Th1-, Th2- and CD8+ cytotoxic T cells. This infiltration is paralleled by the appearance of circulating HPV16-specific IFNγ-producing T-cells in the blood.

Discussion

Skin tests are commonly used as a simple assay for in vivo measurement of cell mediated immunity. We have validated the use of the skin test assay for the measurement of HPV16 specific cellular immune response against the early antigens E2, E6 and E7 in vivo by comparing the results with that of parallel measurements of T cell reactivity by in vitro assays.

In the group of healthy volunteers early skin reactions appeared between 4 to 12 days after intradermal antigen challenge. In these individuals, known to display HPV16 specific type 1 T cell responses in vitro (de Jong, 2002; Welters, 2003), the appearance of an early skin reaction (within 13 days) was significantly associated with the detection of IFNγ-producing HPV16-specific T cells at a frequency of at least 1 per 20.000 PBMC (FIG. 6, p<0.001). The same cut-off criteria for a positive reaction in the IFNγ ELIspot assay are recommended by Jeffries et al (Jeffries, 2006), who used mathematical tools to define the appropriate cut-off of the ELISPOT in relation to Mantoux-tests. The low number of circulating memory T cells (FIG. 6) may explain why the skin reactions appear somewhat delayed compared to classical DTH tests. The T cells need to be boosted or reactivated and start to divide before enough cells are produced to cause a local inflammatory reaction: the positive skin test. Indeed, at the time a positive skin reaction appears, a higher frequency of HPV16-specific Th1 responses can be detected in the peripheral blood (FIG. 7).

Historically it has been postulated that the Th1 cell induce DTH responses, however, several studies have now shown that also Th2 cells infiltrating the skin test sites (Wang, 1999; Woodfolk, 2001). Similarly, this study shows that the positive skin test sites of healthy volunteers contain both Th1 and Th2 type HPV16-specific T cells (FIGS. 8 and 9). In addition, positive skin reactions may also be the result of the influx of non-specific T cells as became evident from two in depth studies of positive skin test sites used to assay the specific immune response following vaccination of patients with renal cell cancer or melanoma (Bleumer, 2007). Also this study showed that a number of positive skin test sites from healthy subjects were infiltrated with T-cells that did not respond to the injected HPV16 antigens. So far, the reason for a-specific positive skin reactions remains unclear. Unexpectedly, we observed the majority of skin reactions in healthy individuals to appear 2 to 3 weeks after intradermal injection of the antigen. While, these late positive skin reactions were not correlated with detection of circulating HPV-specific $CD4^+$ memory T cells in pre-challenge blood (FIG. 6) the immunological constitution of these skin test sites are similar to that of classic DTH tests (Platt, 1983; Poulter, 1982) and comprised of HPV16-specific $CD4^+$ Th1- and Th2-cells as well as HPV16-specific $CD8^+$ T cells (FIGS. 8 and 9). We hypothesize that these reactions might be the result of T cell priming. This has also been noted in 29% of patients whom underwent a 2-step tuberculin skin testing protocol and whom were only positive at the second test round (Akcay, 2003). In general, vaccine-induced T cell responses peak at 10 to 14 days after vaccination and not at three weeks. However, one should bear in mind that in such protocol a higher antigen dose as well as strong adjuvants are injected. It is therefore reasonable to assume that the T cell responses induced by intradermal challenge develop more slowly and peak at a later period. Since the intradermal peptide challenge in healthy volunteers results in the induction of both HPV16-specific $CD4^+$ and $CD8^+$ T cells it, therefore, should be considered as a single, low dose vaccination.

The main objective of this pilot study was to validate the use of the HPV16 specific skin test to detect type 1 immune responses in vivo. In healthy volunteers, a positive skin reaction within 13 days is indeed correlated with the presence of circulating IFNγ-producing memory T cells as detected by the IFNγ ELIspot in vitro. Importantly, we also observed discrepancies between the outcomes obtained by skin test and ELIspot. In a number of cases HPV16-specific circulating IFNγ-producing T cells were detected in the post-challenge blood samples but without a concomitant skin reaction and vice versa (FIG. 7), and this may be considered as a false negative or false positive result. In order to fully understand the impact of this on the interpretation of the detection of type 1 immunity against HPV, we have begun a field trial in a large group of HPV positive patients and healthy volunteers in Indonesia.

REFERENCES LIST

Akcay, A., Erdem, Y., Altun, B., Usalan, C., Agca, E., Yasavul, U., Turgan, C., and Caglar, S. The booster phenomenon in 2-step tuberculin skin testing of patients receiving long-term hemodialysis. Am. J. Infect. Control, 31: 371-374, 2003.

Altmann et al., Eur J Cancer 28:326-33, 1992.

Alvarez D. et al, J. of Immunology, 174:1664-1674, 2005

Bacchetta, R., Sartirana, C., Levings, M. K., Bordignon, C., Narula, S., and Roncarolo, M. G. Growth and expansion of human T regulatory type 1 cells are independent from TCR activation but require exogenous cytokines. Eur J Immunol, 32: 2237-2245, 2002.

Bethwaite, P. B., Holloway, L. J., Thornton, A., and Delahunt, B. Infiltration by immunocompetent cells in early stage invasive carcinoma of the uterine cervix: a prognostic study. Pathology, 28: 321-327, 1996.

Bleumer, I., Tiemessen, D. M., Oosterwijk-Wakka, J. C., Voller, M. C., De Weijer, K., Mulders, P. F., and Oosterwijk, E. Preliminary analysis of patients with progressive renal cell carcinoma vaccinated with CA9-peptide-pulsed mature dendritic cells. J. Immunother., 30: 116-122, 2007.

Bontkes, H. J., de Gruijl, T. D., van den Muysenberg, A. J., Verheijen, R. H., Stukart, M. J., Meijer, C. J., Scheper, R. J., Stacey, S. N., Duggan-Keen, M. F., Stern, P. L., Man, S., Borysiewicz, L. K., and Walboomers, J. M. Human papillomavirus type 16 E6/E7-specific cytotoxic T lymphocytes in women with cervical neoplasia. Int J Cancer, 88: 92-98, 2000.

Bosch, F. X. and de Sanjose, S. Chapter 1: Human papillomavirus and cervical cancer-burden and assessment of causality. J Natl Cancer Inst Monogr: 3-13, 2003.

Bosch, F. X., Manos, M. M., Munoz, N., Sherman, M., Jansen, A. M., Peto, J., Schiffman, M. H., Moreno, V., Kurman, R., and Shah, K. V. Prevalence of human papillomavirus in cervical cancer: a worldwide perspective. International biological study on cervical cancer (IBSCC) Study Group. J Natl Cancer Inst, 87: 796-802, 1995.

Chao, H. T., Wang, P. H., Tseng, J. Y., Lai, C. R., Chiang, S. C., and Yuan, C. C. Lymphocyte-infiltrated FIGO Stage IIB squamous cell carcinoma of the cervix is a prominent factor for disease-free survival. Eur J Gynaecol Oncol, 20: 136-140, 1999.

Claas, E. C., Melchers, W. J., van der Linden, H. C., Lindeman, J., and Quint, W. G. Human papillomavirus detection in paraffin-embedded cervical carcinomas and metastases of the carcinomas by the polymerase chain reaction. Am J Pathol, 135: 703-709, 1989.

de Jong, A., van der Burg, S. H., Kwappenberg, K. M., van der Hulst, J. M., Franken, K. L., Geluk, A., van Meijgaarden, K. E., Drijfhout, J. W., Kenter, G., Vermeij, P., Melief, C. J., and Offringa, R. Frequent detection of human papillomavirus 16 E2-specific T-helper immunity in healthy subjects. Cancer Res, 62: 472-479, 2002.

de Jong, A., van der Hulst, J. M., Kenter, G. G., Drijfhout, J. W., Franken, K. L., Vermeij, P., Offringa, R., van der Burg, S. H., and Melief, C. J. Rapid enrichment of human papillomavirus (HPV)-specific polyclonal T cell populations for adoptive immunotherapy of cervical cancer. Int J Cancer, 114: 274-282, 2005.

de Jong, A., van Poelgeest, M. I., van der Hulst, J. M., Drijfhout, J. W., Fleuren, G. J., Melief, C. J., Kenter, G., Offringa, R., and van der Burg, S. H. Human papillomavirus type 16-positive cervical cancer is associated with impaired CD4+ T-cell immunity against early antigens E2 and E6. Cancer Res, 64: 5449-5455, 2004.

De Witte et al., Blood, August 1; 108(3):870-7, 2006

Evans, M., Borysiewicz, L. K., Evans, A. S., Rowe, M., Jones, M., Gileadi, U., Cerundolo, V., and Man, S. Antigen processing defects in cervical carcinomas limit the presentation of a CTL epitope from human papillomavirus 16 E6. J Immunol, 167: 5420-5428, 2001.

Evans, E. M., Man, S., Evans, A. S., and Borysiewicz, L. K. Infiltration of cervical cancer tissue with human papillomavirus-specific cytotoxic T-lymphocytes. Cancer Res, 57: 2943-2950, 1997.

Facchinetti, V., Seresini, S., Longhi, R., Garavaglia, C., Casorati, G., and Protti, M. P. CD4+ T cell immunity against the human papillomavirus-18 E6 transforming protein in healthy donors: identification of promiscuous naturally processed epitopes. Eur J Immunol, 35: 806-815, 2005.

Geginat, J., Sallusto, F., and Lanzavecchia, A. Cytokine-driven proliferation and differentiation of human naive, central memory, and effector memory CD4(+) T cells. J Exp Med, 194: 1711-1719, 2001.

Hilders, C. G., Houbiers, J. G., Krul, E. J., and Fleuren, G. J. The expression of histocompatibility-related leukocyte antigens in the pathway to cervical carcinoma. Am J Clin Pathol, 101: 5-12, 1994.

Hohn, H., Pilch, H., Gunzel, S., Neukirch, C., Hilmes, C., Kaufmann, A., Seliger, B., and Maeurer, M. J. CD4+ tumor-infiltrating lymphocytes in cervical cancer recognize HLA-DR-restricted peptides provided by human papillomavirus-E7. J Immunol, 163: 5715-5722, 1999.

Hohn, H., Pilch, H., Gunzel, S., Neukirch, C., Freitag, K., Necker, A., and Maeurer, M. J. Human papillomavirus type 33 E7 peptides presented by HLA-DR*0402 to tumor-infiltrating T cells in cervical cancer. J Virol, 74: 6632-6636, 2000.

Hopfl, R., Heim, K., Christensen, N., Zumbach, K., Wieland, U., Volgger, B., Widschwendter, A., Haimbuchner, S., Muller-Holzner, E., Pawlita, M., Pfister, H., and Fritsch, P. Spontaneous regression of CIN and delayed-type hypersensitivity to HPV 16 oncoprotein E7. Lancet, 356: 1985-1986, 2000.

Hopfl, R., Sandbichler, M., Sepp, N., Heim, K., Muller-Holzner, E., Wartusch, B., Dapunt, O., Jochmus-Kudielka, I., ter Meulen, J., Gissmann, L., and. Skin test for HPV type 16 proteins in cervical intraepithelial neoplasia. Lancet, 337: 373-374, 1991.

Jeffries, D. J., Hill, P. C., Fox, A., Lugos, M., Jackson-Sillah, D. J., Adegbola, R. A., and Brookes, R. H. Identifying ELISPOT and skin test cut-offs for diagnosis of *Mycobacterium tuberculosis* infection in The Gambia. Int. J. Tuberc. Lung Dis., 10: 192 198, 2006.

Kessler et al., Hum Immunol. 64:245, 2003.

Lanzavecchia, Nature 393:413, 1998

Lambeck, A. J. A., Leffer, N., Hoogeboom, B. N., Sluiter, W. J., MHamming, L. E., Klip, H., ten Hoor, K. A., Esajas, M., van Oven, M., Drijfhout, J. W., Platteel, I., Offringa, R., Hollema, H., Melief, C. J. M., van der Burg, S. H., van der Zee, A. G. J., Daemen, T., and Nijman, H. W. P53-specific T cell responses in patients with malignant and benign ovarian tumors: implications for p53 based immunotherapy. Int J Cancer, in press, 2007.

Li, J., Huston, G., and Swain, S. L. IL-7 promotes the transition of CD4 effectors to persistent memory cells. J Exp Med, 198: 1807-1815, 2003.

Li, X. C., Demirci, G., Ferrari-Lacraz, S., Groves, C., Coyle, A., Malek, T. R., and Strom, T. B. IL-15 and IL-2: a matter of life and death for T cells in vivo. Nat Med, 7: 114-118, 2001.

Liu, K., Catalfamo, M., Li, Y., Henkart, P. A., and Weng, N. P. IL-15 mimics T cell receptor crosslinking in the induction of cellular proliferation, gene expression, and cytotoxicity in CD8+ memory T cells. Proc Natl Acad Sci USA, 99: 6192-6197, 2002.

Luxton, J. C., Rowe, A. J., Cridland, J. C., Coletart, T., Wilson, P., and Shepherd, P. S. Proliferative T cell responses to the human papillomavirus type 16 E7 protein in women with cervical dysplasia and cervical carcinoma and in healthy individuals. J Gen Virol, 77 (Pt 7): 1585-1593, 1996.

McKinlay, A., Radford, K., Kato, M., Field, K., Gardiner, D., Khalil, D., Burnell, F., Hart, D., and Vuckovic, S. Blood monocytes, myeloid dendritic cells and the cytokines interleukin (IL)-7 and IL-15 maintain human CD4+T memory cells with mixed helper/regulatory function. Immunology, 120: 392-403, 2007.

Munoz, N., Bosch, F. X., de Sanjose, S., Herrero, R., Castellsague, X., Shah, K. V., Snijders, P. J., and Meijer, C. J. Epidemiologic classification of human papillomavirus types associated with cervical cancer. N Engl J Med, 348: 518-527, 2003.

Nakagawa, M., Kim, K. H., Gillam, T. M., and Moscicki, A. B. HLA class I binding promiscuity of the CD8 T-cell epitopes of human papillomavirus type 16 E6 protein. J Virol, 81: 1412-1423, 2007.

Nakagawa, M., Kim, K. H., and Moscicki, A. B. Different methods of identifying new antigenic epitopes of human papillomavirus type 16 E6 and E7 proteins. Clin Diagn Lab Immunol, 11: 889-896, 2004.

Oerke, S., Hohn, H., Zehbe, I., Pilch, H., Schicketanz, K. H., Hitzler, W. E., Neukirch, C., Freitag, K., and Maeurer, M. J. Naturally processed and HLA-B8-presented HPV16 E7 epitope recognized by T cells from patients with cervical cancer. Int J Cancer, 114: 766-778, 2005.

Peng, S., Trimble, C., Ji, H., He, L., Tsai, Y. C., Macaes, B., Hung, C. F., and Wu, T. C. Characterization of HPV-16 E6 DNA vaccines employing intracellular targeting and intercellular spreading strategies. J Biomed Sci, 12: 689-700, 2005.

Piersma, S. J., Jordanova, E. S., van Poelgeest, M. I., Kwappenberg, K. M., van der Hulst, J. M., Drijfhout, J. W., Melief, C. J., Kenter, G. G., Fleuren, G. J., Offringa, R., and van der Burg, S. H. High number of intraepithelial CD8+ tumor-infiltrating lymphocytes is associated with the absence of lymph node metastases in patients with large early-stage cervical cancer. Cancer Res, 67: 354-361, 2007.

Platt, J. L., Grant, B. W., Eddy, A. A., and Michael, A. F. Immune cell populations in cutaneous delayed-type hypersensitivity. J. Exp. Med., 158: 1227-1242, 1983.

Poulter, L. W., Seymour, G. J., Duke, O., Janossy, G., and Panayi, G. Immunohistological analysis of delayed-type hypersensitivity in man. Cell Immunol., 74: 358-369, 1982.

Remington; The Science and Practice of Pharmacy, 21$^{st}$ Edition 2005, University of Sciences in Philadelphia.

Ressing, M. E., van Driel, W. J., Celis, E., Sette, A., Brandt, M. P., Hartman, M., Anholts, J. D., Schreuder, G. M., ter Harmsel, W. B., Fleuren, G. J., Trimbos, B. J., Kast, W. M., and Melief, C. J. Occasional memory cytotoxic T-cell responses of patients with human papillomavirus type 16-positive cervical lesions against a human leukocyte antigen-A *0201-restricted E7-encoded epitope. Cancer Res, 56: 582-588, 1996.

Romani N. et al, Springer Semin Immunopathol., 13:265-279, 1992.

Schwartz, B. D. Diversity and regulation of expression of human leukocyte antigen class II molecules. Am J Med, 85: 6-8, 1988.

Schumacher et al., Nat Rev Immunol. 2(7):512-9, July 2002.

Strang et al., J Gen Virol. 71:423-31, 1990

Toes et al., Proc. Natl. Acad. Sci. U.S.A 93:7855, 1996
Toes et al., J. Immunol. 156:3911, 1996
van den Burg et al., Hum Immunol. 44:189-198, 1995
van der Burg, S. H., Kwappenberg, K. M., Geluk, A., van der Kruk, M., Pontesilli, O., Hovenkamp, E., Franken, K. L., van Meijgaarden, K. E., Drijfhout, J. W., Ottenhoff, T. H., Melief, C. J., and Offringa, R. Identification of a conserved universal Th epitope in HIV-1 reverse transcriptase that is processed and presented to HIV-specific CD4+ T cells by at least four unrelated HLA-DR molecules. J Immunol, 162: 152-160, 1999.
van der Burg, S. H., Piersma, S. J., de Jong, A., van der Hulst, J. M., Kwappenberg, K. M., van den Hende, M., Welters, M. J., Fleuren, G. J., Melief, C. J. M., Kenter, G., and Offringa, R. Association of cervical cancer with the presence of CD4+ regulatory T cells specific for human papillomavirus antigens. submitted, 2007.
van der Burg, S. H., Ressing, M. E., Kwappenberg, K. M., de Jong, A., Straathof, K., de Jong, J., Geluk, A., van Meijgaarden, K. E., Franken, K. L., Ottenhoff, T. H., Fleuren, G. J., Kenter, G., Melief, C. J., and Offringa, R. Natural T-helper immunity against human papillomavirus type 16 (HPV16) E7-derived peptide epitopes in patients with HPV16-positive cervical lesions: identification of 3 human leukocyte antigen class II-restricted epitopes. Int J Cancer, 91: 612-618, 2001.
Wang, S., Fan, Y., Brunham, R. C., and Yang, X. IFN-gamma knockout mice show Th2-associated delayed-type hypersensitivity and the inflammatory cells fail to localize and control chlamydial infection. Eur. J. Immunol., 29: 3782-3792, 1999.
Warrino, D. E., Olson, W. C., Knapp, W. T., Scarrow, M. I., D'Ambrosio-Brennan, L. J., Guido, R. S., Edwards, R. P., Kast, W. M., and Storkus, W. J. Disease-stage variance in functional CD4(+) T-cell responses against novel pan-human leukocyte antigen-D region presented human papillomavirus-16 E7 epitopes. Clin Cancer Res, 10: 3301-3308, 2004.
Welters, M. J., van der Logt, P., van den Eeden, S. J., Kwappenberg, K. M., Drijfhout, J. W., Fleuren, G. J., Kenter, G. G., Melief, C. J., van der Burg, S. H., and Offringa, R. Detection of human papillomavirus type 18 E6 and E7-specific CD4+T-helper 1 immunity in relation to health versus disease. Int J Cancer, 118: 950-956, 2006.
Welters, M. J., de Jong, A., van den Eeden, S. J., van der Hulst, J. M., Kwappenberg, K. M., Hassane, S., Franken, K. L., Drijfhout, J. W., Fleuren, G. J., Kenter, G., Melief, C. J., Offringa, R., and van der Burg, S. H. Frequent display of human papillomavirus type 16 E6-specific memory t-Helper cells in the healthy population as witness of previous viral encounter. Cancer Res, 63: 636-641, 2003.
Woodfolk, J. A. and Platts-Mills, T. A. Diversity of the human allergen-specific T cell repertoire associated with distinct skin test reactions: delayed-type hypersensitivity-associated major epitopes induce Th1- and Th2-dominated responses. J. Immunol., 167: 5412-5419, 2001.
zur Hausen, H. Papillomavirus infections—a major cause of human cancers. Biochim Biophys Acta, 9: F55-78, 1996.
Zwaveling, S., Ferreira Mota, S. C., Nouta, J., Johnson, M., Lipford, G. B., Offringa, R., van der Burg, S. H., and Melief, C. J. Established human papillomavirus type 16-expressing tumors are effectively eradicated following vaccination with long peptides. J Immunol, 169: 350-358, 2002.

TABLE 1

HPV16 and 18-specific responses detected in infiltrating lymphocytes.

| HPV Status | Origin | Patient | Age | Cell Type | Stage of disease | Reactivity | SI* | No. peptides recognized | Type of T cell |
|---|---|---|---|---|---|---|---|---|---|
| HPV16 | TIL | 176 | 45 | squamous | FIGO 1B | E6 | 80 | 2 | CD4/CD8 |
|  |  | 178 | 40 | squamous | FIGO 1B | E7 | 11 | 1 | CD4 |
|  |  | 185 | 56 | squamous | FIGO 3B | E7 | 6 | 1 | CD8 |
|  |  | 192 | 37 | squamous | FIGO 1B |  |  |  |  |
|  |  | 194 | 67 | adeno | FIGO 2A | E7 | 5 |  |  |
|  |  | 226 | 56 | squamous | FIGO 1B | E6 | 3 | 1 | CD4 |
|  |  | 229 | 42 | squamous | FIGO 1B |  |  |  |  |
|  |  | 230 | 45 | squamous | FIGO 1A |  |  |  |  |
|  |  | 246 | 31 | squamous | FIGO 1B |  |  |  |  |
|  |  | 265 | 44 | squamous | FIGO 1B | E6 | 104 | 2 | CD4/CD8 |
|  |  | 267 | 49 | squamous | FIGO 1B | E6 | 109 | 2 | CD4 |
|  |  | 271 | 40 | squamous | FIGO 1B |  |  |  |  |
|  |  | 281 | 35 | squamous | FIGO 1B |  |  |  |  |
|  |  | 283 | 51 | squamous | FIGO 1B |  |  |  |  |
|  |  | 308 | 39 | squamous | FIGO 1B |  |  |  |  |
|  |  | 312 | 30 | adeno | FIGO 1B |  |  |  |  |
|  |  | 331 | 65 | squamous | FIGO 1B | E6 | 3 | 2 | CD4/CD8 |
|  |  | 332 | 32 | squamous | FIGO 1B |  |  |  |  |
|  |  | 334 | 41 | squamous | FIGO 1B | E6 | 5 | 1 | CD8 |
|  |  | 338 | 34 | squamous | FIGO 1B |  |  |  |  |
|  |  | 340 | 29 | squamous | FIGO 1B |  |  |  |  |
|  |  | 343 | 51 | unknown | FIGO 1B |  |  |  |  |
|  |  | 344 | 43 | squamous | FIGO 2A |  |  |  |  |
|  |  | 363 | 45 | squamous | FIGO 1B |  |  |  |  |
|  |  | 369 | 33 | adeno | FIGO 1A |  |  |  |  |
|  |  | 371 | 31 | squamous | FIGO 1B |  |  |  |  |
|  |  | 372 | 72 | squamous | FIGO 1B |  |  |  |  |
|  |  | 390 | 33 | adeno | FIGO 1B | E6/E7 | 4 |  |  |
|  |  | 398 | 48 | squamous | FIGO 1B |  |  |  |  |
|  |  | 405 | 41 | squamous | FIGO 2B |  |  |  |  |
|  |  | 418 | 34 | squamous | FIGO 1B |  |  |  |  |
|  |  | 415 | 46 | squamous | FIGO 1B |  |  |  |  |
|  |  | 424 | 35 | squamous | FIGO 1B |  |  |  |  |

TABLE 1-continued

HPV16 and 18-specific responses detected in infiltrating lymphocytes.

| HPV Status | Origin | Patient | Age | Cell Type | Stage of disease | Reactivity | SI* | No. peptides recognized | Type of T cell |
|---|---|---|---|---|---|---|---|---|---|
| | | 441 | 51 | squamous | FIGO 1B | | | | |
| | | 446 | 29 | squamous | FIGO 1B | E6 | 4 | 4 | CD4/CD8 |
| | CIL | 279 | 60 | unknown | CIN3 | | | | |
| | | 284 | 36 | squamous | CIN2 | E7 | 13 | 1 | CD4 |
| | | 285 | 27 | squamous | CIN3 | | | | |
| | | 310 | 46 | squamous | CIN3 | | | | |
| | | 314 | 34 | squamous | CIN3 | E7 | 11 | | |
| | | 355 | 47 | squamous | CIN3 | | | | |
| | | 356 | 26 | squamous | CIN3 | E7 | 3.5 | 1 | CD4 |
| | LN | 148 | 46 | squamous | FIGO 1B | E6/E7 | 9/3 | | CD4 |
| | | 267 | 49 | squamous | FIGO 1B | E6 | 4 | | CD4 |
| | | 271 | 40 | squamous | FIGO 1B | E6/E7 | 1.5/2 | | CD4 |
| | | 427 | 28 | squamous | FIGO 1B | E6 | 9 | | CD4/CD8 |
| HPV18 | TIL | 187 | 43 | squamous | FIGO 1B | E6 | 2 | 1 | CD4 |
| | | 196 | 48 | adenosquamous | FIGO 2A | | | | |
| | | 209 | 55 | squamous | FIGO 1B | | | | |
| | | 214 | 42 | adeno | FIGO 1B | E7 | 15 | 1 | CD4 |
| | | 228 | 37 | squamous | FIGO 2A | E7 | 18 | 1 | CD4 |
| | | 251 | 39 | adenosquamous | FIGO 2A | E7 | 3 | | |
| | | 261 | 38 | squamous | FIGO 1B | | | | |
| | | 335 | 33 | adeno | FIGO 1B | | | | |
| | | 378 | 40 | adeno | FIGO 1B | E7 | 8 | 1 | CD4 |
| | LN | 151 | 43 | squamous | FIGO 1B | E6/E7 | 2/3 | | CD4 |
| HPV16-18- | TIL | 181 | 40 | squamous | FIGO 1B | | | | |
| | | 182 | 80 | squamous | FIGO 2B | | | | |
| | | 215 | 31 | squamous | FIGO 1B | | | | |
| | | 245 | 41 | squamous | FIGO 1B | | | | |
| | | 248 | 46 | squamous | FIGO 2A | | | | |
| | | 264 | 35 | adeno | FIGO 1B | | | | |
| | | 280 | 31 | squamous | FIGO 1B | | | | |
| | | 287 | 61 | carcinosarcome | FIGO 2B | | | | |
| | | 289 | 45 | adeno | FIGO 1B | | | | |
| | | 292 | 32 | squamous | FIGO 1B | | | | |
| | | 324 | 51 | squamous | FIGO 1B | | | | |
| | | 353 | 35 | adeno | FIGO 1A | | | | |
| | | 373 | 55 | squamous | FIGO 1B | | | | |
| | | 377 | 85 | squamous | FIGO 1B | | | | |
| | | 381 | 80 | adeno | FIGO 1B | | | | |
| | | 384 | 75 | squamous | FIGO 1B | | | | |
| | | 414 | 64 | squamous | FIGO 2A | | | | |
| | CIL | 348 | 35 | squamous | CIN3 | | | | |
| | | 354 | 39 | squamous | CIN3 | | | | |
| | LN | 426 | 40 | squamous | FIGO 1B | | | | |

*SI = Stimulation Index of responding T cells

TABLE 2

T-cell epitopes recognized by cervical cancer patients

| T cell type | epitope recognized | restriction | Origin | patient | SEQ ID |
|---|---|---|---|---|---|
| CD4 | HPV16E6.11-32 | DP17 | LN | C148 | 5 |
| | HPV16E6.11-32 | DP1401 | LN | C271, C427 | 5 |
| | HPV16E6.37-68 | DP0201 | TIL | C226 | 6 |
| | HPV16E6.52-61 | DP0201 | TIL | C265 | 7 |
| | HPV16E6.55-86 | unknown | LN,TIL | C267 | 8 |
| | HPV16E6.61-82 | DP1 or DP14 | LN | C427 | 9 |
| | HPV16E6.73-105 | DP4 | LN | C148 | 10 |
| | HPV16E6.73-105 | unknown | LN,TIL | C267 | 10 |
| | HPV16E6.91-112 | DR15 or DQ5 | TIL | C331 | 11 |
| | HPV16E6.91-112 | unknown | LN | C267 | 11 |
| | HPV16E6.101-122 | DQ6 | LN,TIL | C427, C446 | 12 |
| | HPV16E6.121-142 | DP0201 or DQ5 | TIL | C265 | 13 |
| | HPV16E6.121-142 | unknown | TIL | C187 | 13 |
| | HPV16E6.129-138 | DR7 | TIL | C176 | 14 |
| | HPV16E7.21-42 | DR4 | TIL | C178 | 15 |
| | HPV16E7.51-72 | DP1901 | CIL | C356 | 16 |
| | HPV16E7.76-86 | DR12 | CIL | C284 | 17 |
| | HPV18E6.51-72 | DQ*0301 | LN | C151 | 18 |
| | HPV18E6.71-92 | DQ*0501 | LN | C151 | 19 |
| | HPV18E7.1-32 | DQ*0302, DQ*0308 | TIL | C214 | 20 |

TABLE 2-continued

T-cell epitopes recognized by cervical cancer patients

| T cell type | epitope recognized | restriction | Origin | patient | SEQ ID |
|---|---|---|---|---|---|
| CD8 | HPV18E7.1-32 | unknown | TIL | C378 | 20 |
| | HPV18E7.21-42 | DQ*0302 | TIL | C228 | 21 |
| | HPV16E6.13-22 | HLA-B7 | TIL | C446 | 22 |
| | HPV16E6.29-38 | HLA-A2 | LN | C427 | 23 |
| | HPV16E6.52-61 | HLA-B57 | TIL | C331 | 7 |
| | HPV16E6.52-61 | unknown | TIL | C265 | 7 |
| | HPV16E6.129-138 | unknown | TIL | C265 | 14 |
| | HPV16E6.137-146 | HLA-B27 | TIL | C176, C334 | 24 |
| | HPV16E6.149-158 | HLA-B14 | LN | C427 | 25 |
| | HPV16E7.11-19 | HLA*0201 | TIL | C185 | 26 |

The invention claimed is:

1. An immunogenic pharmaceutical composition comprising:
   (a) a peptide having a length of no more than 45 amino acids and comprising at least 31 and no more than 35 contiguous amino acids from the amino acid sequence of an HPV protein, wherein the contiguous amino acid sequence comprises at least one of SEQ ID NOs: 7, 14, 22, 24, 25, or 26; and
   (b) an immune-stimulating amount of a pharmaceutically acceptable adjuvant.

2. The immunogenic pharmaceutical composition according to claim 1, wherein the contiguous amino acid sequence comprises an epitope that is presented by an HLA-B molecule.

3. The immunogenic pharmaceutical composition according to claim 1, wherein the composition comprises at least two different peptides as defined in claim 1.

4. The immunogenic pharmaceutical composition according to claim 1, wherein the pharmaceutically acceptable adjuvant acts via a Toll-like receptor.

5. The immunogenic pharmaceutical composition according to claim 1, wherein the composition is for intravenous, subcutaneous, intramuscular, mucosal, intradermal and/or intracutaneous administration.

6. The immunogenic pharmaceutical composition according to claim 1 for the treatment or prevention of an HPV related disease.

7. The immunogenic pharmaceutical composition according to claim 5, wherein the HPV related disease is selected from the group consisting of: cervical intraepithelial neoplasia of the cervix (CIN), vulva (VIN), vagina (VaIN), anus (AIN), and penis (PIN) and cancer of the cervix, vulva, vagina, anus, penis and head & neck.

8. The immunogenic pharmaceutical composition according to claim 1, wherein the pharmaceutically acceptable adjuvant is synthetic.

9. The immunogenic pharmaceutical composition according to claim 4, wherein the pharmaceutically acceptable adjuvant is selected from the group consisting of: Gram positive bacterial glycolipids, fimbriae, outer membrane proteins, heat shock proteins, mycobacterial lipoarabinomannans, dsRNA, poly(I:C), Gram negative glycolipids, viral coat or envelope proteins, taxol or derivatives thereof, hyaluronan containing oligosaccharides or fibronectins, bacterial flagellae or flagellin, mycobacterial lipoproteins, group B *Streptococcus* heat labile soluble factor (GBS-F), *Staphylococcus* modulins, and imidazoquinolines.

10. The immunogenic pharmaceutical composition according to claim 1, wherein the pharmaceutically acceptable adjuvant is selected from the group consisting of:
   dsRNA, poly(I:C), unmethylated CpG DNA, IC31, IMSAVAC, Montanide ISA-51 and Montanide ISA 720.

11. The immunogenic pharmaceutical composition according to claim 1, wherein the pharmaceutically acceptable adjuvant is physically linked to the peptide.

12. The immunogenic pharmaceutical composition according to claim 1, further comprising at least one immune modulator.

13. The immunogenic pharmaceutical composition according to claim 1, further comprising at least one additional peptide having a length of no more than 100 amino acids and comprising at least 19 contiguous amino acids from the amino acid sequence of at least one of an HPV E6 and E7 protein, wherein the contiguous amino acid sequence of the additional peptide comprises an epitope that is recognized by a T cell that infiltrates a cervical neoplastic lesion or by a T cell from a draining lymph node.

14. The immunogenic pharmaceutical composition according to claim 13, wherein the epitope of the additional peptide is selected from the group consisting of SEQ ID NO: 5, 6, 8, 9, 10, 11, 12, 13, 15, 16, 17, 18, 19, 20, 21, and 23.

15. The immunogenic pharmaceutical composition according to claim 1, wherein the peptide comprises SEQ ID NO: 34.

16. The immunogenic pharmaceutical composition according to claim 1, wherein the peptide consists of SEQ ID NO: 34.

17. The immunogenic pharmaceutical composition according to claim 1, wherein the peptide comprises SEQ ID NO: 35.

18. The immunogenic pharmaceutical composition according to claim 1, wherein the peptide consists of SEQ ID NO: 35.

19. The immunogenic pharmaceutical composition according to claim 1, wherein the HLA-B molecule is an HLA-B7, HLA-B14, HLA-B27 or HLA-B57 molecule.

* * * * *